US010166332B2

(12) United States Patent
Miller et al.

(10) Patent No.: US 10,166,332 B2
(45) Date of Patent: *Jan. 1, 2019

(54) APPARATUS TO INJECT FLUIDS INTO BONE MARROW AND OTHER TARGET SITES

(71) Applicant: TELEFLEX MEDICAL DEVICES S.A R.L., Luxembourg (LU)

(72) Inventors: Larry J. Miller, Spring Branch, TX (US); David S. Bolleter, San Antonio, TX (US); Charles M. Schwimmer, Los Gatos, CA (US); Robert A. Wilk, Sierra Village, CA (US)

(73) Assignee: TELEFLEX MEDICAL DEVICES S.À R.L., Luxembourg (LU)

( * ) Notice: Subject to any disclaimer, the term of this patent is extended or adjusted under 35 U.S.C. 154(b) by 189 days.

This patent is subject to a terminal disclaimer.

(21) Appl. No.: 15/064,272

(22) Filed: Mar. 8, 2016

(65) Prior Publication Data

US 2016/0184509 A1  Jun. 30, 2016

Related U.S. Application Data

(60) Continuation of application No. 12/718,638, filed on Mar. 5, 2010, now Pat. No. 9,295,487, which is a
(Continued)

(51) Int. Cl.
*A61M 5/145* (2006.01)
*A61B 17/32* (2006.01)
(Continued)

(52) U.S. Cl.
CPC ..... *A61M 5/1454* (2013.01); *A61B 17/32002* (2013.01); *A61B 17/3472* (2013.01);
(Continued)

(58) Field of Classification Search
CPC ............. A61M 5/1454; A61M 5/2033; A61M 2005/3289; A61M 2210/02; A61B 17/3472; A61B 17/32002
See application file for complete search history.

(56) References Cited

U.S. PATENT DOCUMENTS

| 1,539,637 A | 5/1925 | Bronner |
| 1,954,620 A | 4/1934 | Connell |

(Continued)

FOREIGN PATENT DOCUMENTS

| CA | 2138842 | 6/1996 |
| CA | 2 454 600 | 1/2004 |

(Continued)

OTHER PUBLICATIONS

International Preliminary Report on Patentabilty, PCT/US2007/072202, 10 pages, dated Jan. 15, 2009.
(Continued)

*Primary Examiner* — Bradley J Osinski
(74) *Attorney, Agent, or Firm* — Baker & Hostetler LLP

(57) ABSTRACT

The present disclosure relates to an apparatus for delivering a quantity of fluid to bone marrow. The apparatus may include a drive housing, a plunger operating assembly, a retractable sleeve, a first spring, a second spring, and a release mechanism. The drive housing may include a first portion configured to engage a driver assembly and a second portion configured to engage a cartridge assembly. The cartridge assembly may a fluid reservoir and a plunger assembly slidably disposed in the fluid reservoir. The cartridge assembly may be engaged with a bone penetrating needle and configured to rotate to insert the bone penetrating needle into the bone marrow. The first release mechanism may release the second spring to move the plunger operating assembly when the cartridge assembly is rotated to insert the
(Continued)

bone penetrating needle into the bone marrow and the retractable sleeve is moved to a retracted position.

20 Claims, 14 Drawing Sheets

Related U.S. Application Data division of application No. 12/347,506, filed on Dec. 31, 2008, now Pat. No. 8,038,664, which is a division of application No. 11/190,331, filed on Jul. 27, 2005, now Pat. No. 7,811,260, which is a continuation-in-part of application No. 10/449,503, filed on May 30, 2003, now Pat. No. 7,670,328.

(60) Provisional application No. 60/384,756, filed on May 31, 2002.

(51) Int. Cl.
| | |
|---|---|
| A61B 90/00 | (2016.01) |
| A61B 17/3205 | (2006.01) |
| A61B 17/34 | (2006.01) |
| A61M 5/158 | (2006.01) |
| A61M 5/20 | (2006.01) |
| A61M 5/24 | (2006.01) |
| A61M 5/315 | (2006.01) |
| A61M 5/32 | (2006.01) |
| A61M 5/34 | (2006.01) |
| A61M 5/31 | (2006.01) |
| A61B 90/11 | (2016.01) |

(52) U.S. Cl.
CPC .... *A61B 17/3476* (2013.01); *A61B 17/32053* (2013.01); *A61B 17/3403* (2013.01); *A61B 90/11* (2016.02); *A61B 2017/3413* (2013.01); *A61B 2090/034* (2016.02); *A61M 5/158* (2013.01); *A61M 5/2033* (2013.01); *A61M 5/24* (2013.01); *A61M 5/31511* (2013.01); *A61M 5/3291* (2013.01); *A61M 5/34* (2013.01); *A61M 2005/1581* (2013.01); *A61M 2005/1585* (2013.01); *A61M 2005/3103* (2013.01); *A61M 2005/3289* (2013.01); *A61M 2210/02* (2013.01)

(56) References Cited

U.S. PATENT DOCUMENTS

| | | | |
|---|---|---|---|
| 2,317,648 A | 4/1943 | Siqveland | |
| 2,419,045 A | 4/1947 | Whittaker | |
| 2,766,907 A | 10/1956 | Wallace, Jr. | |
| 2,773,501 A | 12/1956 | Young | |
| 2,660,635 A | 11/1958 | Wilburn | |
| 3,104,448 A | 9/1963 | Morrow et al. | |
| 3,120,845 A | 2/1964 | Horner | |
| 3,173,417 A | 3/1965 | Horner | |
| 3,175,554 A | 3/1965 | Stewart | |
| 3,507,276 A | 4/1970 | Burgess et al. | |
| 3,529,580 A | 9/1970 | Stevens | |
| 3,543,966 A | 12/1970 | Ryan et al. | |
| 3,697,223 A | 10/1972 | Kovalcik | |
| 3,734,207 A | 5/1973 | Fishbein | |
| 3,750,667 A | 8/1973 | Pshenichny et al. | |
| 3,802,555 A | 4/1974 | Grasty et al. | |
| 3,815,605 A | 6/1974 | Schmidt et al. | |
| 3,835,860 A | 9/1974 | Garretson | |
| 3,893,445 A | 7/1975 | Hofsess | |
| 3,935,909 A | 2/1976 | Mabuchi et al. | |
| 3,991,765 A | 11/1976 | Cohen | |
| 4,021,920 A | 5/1977 | Kirschner et al. | |
| 4,099,518 A | 7/1978 | Baylis et al. | |
| 4,124,026 A | 11/1978 | Berner et al. | |
| 4,142,517 A | 3/1979 | Stavropoulos et al. | |
| 4,170,993 A | 10/1979 | Alvarez | |
| 4,185,619 A | 1/1980 | Reiss | |
| 4,194,505 A | 3/1980 | Schmitz | |
| 4,258,722 A | 3/1981 | Sessions et al. | |
| 4,262,676 A | 4/1981 | Jamshidi | |
| 4,266,555 A | 5/1981 | Jamshidi | |
| 4,306,570 A | 12/1981 | Matthews | |
| 4,333,459 A * | 6/1982 | Becker | A61M 5/20 604/117 |
| 4,359,052 A | 11/1982 | Staub | |
| 4,381,777 A | 5/1983 | Garnier | |
| 4,399,723 A | 8/1983 | Marleau | |
| 4,413,760 A * | 11/1983 | Paton | A61M 5/3158 222/309 |
| 4,420,085 A | 12/1983 | Wilson et al. | |
| 4,441,563 A | 4/1984 | Walton, II | |
| 4,469,109 A | 9/1984 | Mehl | |
| 4,484,577 A | 11/1984 | Sackner et al. | |
| 4,487,209 A | 12/1984 | Mehl | |
| 4,504,267 A | 3/1985 | Parmelee et al. | |
| 4,543,966 A | 10/1985 | Islam et al. | |
| 4,553,539 A | 11/1985 | Morris | |
| 4,578,064 A | 3/1986 | Sarnoff et al. | |
| 4,605,011 A | 8/1986 | Naslund | |
| 4,620,539 A | 11/1986 | Andrews et al. | |
| 4,630,616 A | 12/1986 | Tretinyak | |
| 4,646,731 A | 3/1987 | Brower | |
| 4,654,492 A | 3/1987 | Koerner et al. | |
| 4,655,226 A | 4/1987 | Lee | |
| 4,659,329 A | 4/1987 | Annis | |
| 4,692,073 A | 9/1987 | Martindell | |
| 4,711,636 A | 12/1987 | Bierman | |
| 4,713,061 A | 12/1987 | Tarello et al. | |
| 4,716,901 A | 1/1988 | Jackson et al. | |
| 4,723,945 A | 2/1988 | Theiling | |
| 4,736,850 A | 4/1988 | Bowman et al. | |
| 4,758,225 A | 7/1988 | Cox et al. | |
| 4,762,118 A | 8/1988 | Lia et al. | |
| 4,772,261 A | 9/1988 | Von Hoff et al. | |
| 4,787,893 A | 11/1988 | Villette | |
| 4,793,363 A | 12/1988 | Ausherman et al. | |
| 4,838,282 A | 6/1989 | Strasser et al. | |
| 4,844,259 A | 7/1989 | Glowczewskie et al. | |
| 4,867,158 A | 9/1989 | Sugg | |
| 4,919,146 A | 4/1990 | Rhinehart et al. | |
| 4,921,013 A | 5/1990 | Spalink et al. | |
| 4,922,602 A | 5/1990 | Mehl | |
| 4,935,010 A | 6/1990 | Cox et al. | |
| 4,940,459 A | 7/1990 | Noce | |
| 4,944,677 A | 7/1990 | Alexandre | |
| 4,969,870 A | 11/1990 | Kramer et al. | |
| 4,986,279 A | 1/1991 | O'Neill | |
| 5,002,546 A | 3/1991 | Romano | |
| 5,025,797 A | 6/1991 | Baran | |
| 5,036,860 A | 8/1991 | Leigh et al. | |
| 5,057,085 A | 10/1991 | Kopans | |
| 5,074,311 A | 12/1991 | Hasson | |
| 5,116,324 A | 5/1992 | Brierley et al. | |
| 5,120,312 A | 6/1992 | Wigness et al. | |
| 5,122,114 A | 6/1992 | Miller et al. | |
| 5,133,359 A | 7/1992 | Kedem | |
| 5,137,500 A | 8/1992 | Lhotak | |
| 5,137,518 A | 8/1992 | Mersch | |
| 5,139,500 A | 8/1992 | Schwartz | |
| RE34,056 E | 9/1992 | Lindgren et al. | |
| 5,145,369 A | 9/1992 | Lustig et al. | |
| 5,172,701 A | 12/1992 | Leigh | |
| 5,172,702 A | 12/1992 | Leigh et al. | |
| 5,176,415 A | 1/1993 | Choksi | |
| 5,176,643 A | 1/1993 | Kramer et al. | |
| 5,195,985 A | 3/1993 | Hall | |
| 5,203,056 A | 4/1993 | Funk et al. | |
| 5,207,697 A | 5/1993 | Carusillo et al. | |
| 5,249,583 A | 10/1993 | Mallaby | |
| 5,257,632 A | 11/1993 | Turkel et al. | |
| 5,261,877 A | 11/1993 | Fine et al. | |
| 5,269,785 A | 12/1993 | Bonutti | |

(56) References Cited

U.S. PATENT DOCUMENTS

| | | |
|---|---|---|
| 5,271,414 A | 12/1993 | Partika et al. |
| 5,279,306 A | 1/1994 | Mehl |
| 5,312,351 A | 5/1994 | Gerrone |
| 5,312,364 A | 5/1994 | Jacobs |
| 5,312,408 A | 5/1994 | Brown |
| 5,315,737 A | 5/1994 | Ouimet |
| 5,324,300 A | 6/1994 | Elias et al. |
| 5,341,316 A | 6/1994 | Allen |
| 5,330,480 A | 7/1994 | Meloul et al. |
| 5,332,398 A | 7/1994 | Miller et al. |
| 5,333,790 A | 8/1994 | Christopher |
| 5,334,204 A | 8/1994 | Clewett et al. |
| 5,341,823 A | 8/1994 | Manosalva et al. |
| 5,348,022 A | 9/1994 | Legh et al. |
| 5,356,006 A | 10/1994 | Alpern et al. |
| 5,357,974 A | 10/1994 | Baldridge |
| 5,361,853 A | 11/1994 | Takamura et al. |
| 5,368,046 A | 11/1994 | Scarfone et al. |
| 5,372,583 A | 12/1994 | Roberts et al. |
| 5,383,859 A | 1/1995 | Sewell, Jr. |
| 5,385,151 A | 1/1995 | Scarfone et al. |
| 5,385,553 A | 1/1995 | Hart et al. |
| 5,389,553 A | 2/1995 | Grubisich et al. |
| 5,400,798 A | 3/1995 | Baran |
| 5,405,348 A | 4/1995 | Anspach et al. |
| 5,405,362 A | 4/1995 | Kramer et al. |
| 5,423,824 A | 6/1995 | Akerfeldt et al. |
| 5,431,655 A | 7/1995 | Melker et al. |
| 5,451,210 A | 9/1995 | Kramer et al. |
| 5,484,442 A | 1/1996 | Melker et al. |
| 5,505,737 A | 4/1996 | Gosselin et al. |
| D369,858 S | 5/1996 | Baker et al. |
| 5,514,097 A | 5/1996 | Knauer |
| 5,526,821 A | 6/1996 | Jamshidi |
| 5,529,580 A | 6/1996 | Kusunoki et al. |
| 5,549,565 A | 8/1996 | Ryan et al. |
| 5,554,154 A | 9/1996 | Rosenberg |
| 5,556,399 A | 9/1996 | Huebner |
| 5,558,737 A | 9/1996 | Brown et al. |
| 5,571,133 A | 11/1996 | Yoon |
| 5,586,847 A | 12/1996 | Mattern et al. |
| 5,591,188 A | 1/1997 | Waisman |
| 5,595,186 A | 1/1997 | Rubinstein et al. |
| 5,601,559 A | 2/1997 | Melker et al. |
| 5,624,214 A | 4/1997 | Carroll |
| 5,632,747 A | 5/1997 | Scarborough et al. |
| 5,651,419 A | 7/1997 | Holzer et al. |
| 5,672,155 A | 9/1997 | Riley et al. |
| 5,709,275 A | 1/1998 | Neumaier |
| 5,713,368 A | 2/1998 | Leigh |
| 5,724,873 A | 3/1998 | Hillinger |
| 5,733,262 A | 3/1998 | Paul |
| 5,752,923 A | 5/1998 | Terwilliger |
| 5,762,639 A | 6/1998 | Gibbs |
| 5,766,221 A | 6/1998 | Benderev et al. |
| 5,769,086 A | 6/1998 | Ritchart et al. |
| 5,779,708 A | 7/1998 | Wu |
| 5,800,389 A | 9/1998 | Burney et al. |
| 5,807,275 A | 9/1998 | Jamshidi |
| 5,807,277 A | 9/1998 | Swaim |
| 5,810,826 A | 9/1998 | Akerfeldt et al. |
| 5,817,052 A | 10/1998 | Johnson et al. |
| 5,823,970 A | 10/1998 | Terwilliger |
| D403,405 S | 12/1998 | Terwilliger |
| 5,858,005 A | 1/1999 | Kriesel |
| 5,865,711 A | 2/1999 | Kramer et al. |
| 5,868,711 A | 2/1999 | Kramer et al. |
| 5,868,750 A | 2/1999 | Schultz |
| 5,873,499 A | 2/1999 | Leschinsky et al. |
| 5,873,510 A | 2/1999 | Hirai et al. |
| 5,885,226 A | 3/1999 | Rubinstein et al. |
| 5,891,085 A | 4/1999 | Lilley et al. |
| 5,911,701 A | 6/1999 | Miller et al. |
| 5,911,708 A | 6/1999 | Teirstein |
| 5,916,229 A | 6/1999 | Evans |
| 5,919,172 A | 7/1999 | Golba, Jr. |
| 5,921,987 A | 7/1999 | Stone |
| 5,924,864 A | 7/1999 | Loge et al. |
| 5,927,976 A | 7/1999 | Wu |
| 5,928,238 A | 7/1999 | Scarborough et al. |
| 5,938,636 A | 8/1999 | Kramer et al. |
| 5,941,706 A | 8/1999 | Ura |
| 5,941,851 A | 8/1999 | Coffey et al. |
| 5,951,026 A | 9/1999 | Harman et al. |
| 5,960,797 A | 10/1999 | Kramer et al. |
| 5,980,469 A | 11/1999 | Burbank et al. |
| 5,980,545 A | 11/1999 | Pacala et al. |
| 5,984,020 A | 11/1999 | Meyer et al. |
| 5,989,257 A | 11/1999 | Tidwell et al. |
| 5,993,417 A | 11/1999 | Yerfino et al. |
| 5,993,454 A | 11/1999 | Longo |
| 6,007,496 A | 12/1999 | Brannon |
| 6,017,348 A | 1/2000 | Hart et al. |
| 6,018,094 A | 1/2000 | Fox |
| 6,022,324 A | 2/2000 | Skinner |
| 6,027,458 A | 2/2000 | Janssens |
| 6,033,369 A | 3/2000 | Goldenberg |
| 6,033,411 A | 3/2000 | Preissman |
| 6,063,037 A | 5/2000 | Mittermeier et al. |
| 6,071,284 A | 6/2000 | Fox |
| 6,080,115 A | 6/2000 | Rubinstein et al. |
| 6,083,176 A | 7/2000 | Terwilliger |
| 6,086,543 A | 7/2000 | Anderson et al. |
| 6,086,544 A | 7/2000 | Hibner et al. |
| 6,096,042 A | 8/2000 | Herbert |
| 6,102,915 A | 8/2000 | Bresier et al. |
| 6,106,484 A | 8/2000 | Terwilliger |
| 6,110,128 A | 8/2000 | Andelin et al. |
| 6,110,129 A | 8/2000 | Terwilliger |
| 6,110,174 A | 8/2000 | Nichter |
| 6,120,462 A | 9/2000 | Hibner et al. |
| 6,126,670 A | 10/2000 | Walker et al. |
| 6,135,769 A | 10/2000 | Kwan |
| 6,159,163 A | 12/2000 | Strauss et al. |
| 6,162,203 A | 12/2000 | Haaga |
| 6,183,442 B1 | 2/2001 | Athanasiou et al. |
| 6,210,376 B1 | 4/2001 | Grayson |
| 6,217,561 B1 | 4/2001 | Gibbs |
| 6,221,029 B1 | 4/2001 | Mathis et al. |
| 6,228,049 B1 | 5/2001 | Schroeder et al. |
| 6,228,088 B1 | 5/2001 | Miller et al. |
| 6,238,355 B1 | 5/2001 | Daum |
| 6,247,928 B1 | 6/2001 | Meller et al. |
| 6,248,110 B1 | 6/2001 | Reiley et al. |
| 6,257,351 B1 | 7/2001 | Ark et al. |
| 6,267,763 B1 | 7/2001 | Castro |
| 6,270,087 B1 | 8/2001 | Mickel et al. |
| 6,273,715 B1 | 8/2001 | Meller et al. |
| 6,273,862 B1 | 8/2001 | Privitera et al. |
| 6,283,925 B1 | 9/2001 | Terwilliger |
| 6,283,970 B1 | 9/2001 | Lubinus |
| 6,287,114 B1 | 9/2001 | Meller et al. |
| 6,302,852 B1 | 10/2001 | Fleming et al. |
| 6,309,358 B1 | 10/2001 | Okubo |
| 6,312,394 B1 | 11/2001 | Fleming |
| 6,315,737 B1 | 11/2001 | Skinner |
| 6,325,806 B1 | 12/2001 | Fox |
| 6,328,701 B1 | 12/2001 | Terwilliger |
| 6,328,744 B1 | 12/2001 | Harari et al. |
| 6,358,252 B1 | 3/2002 | Shapira |
| 6,402,701 B1 | 6/2002 | Kaplan et al. |
| 6,419,490 B1 | 7/2002 | Kitchings Weathers, Jr. |
| 6,425,388 B1 | 7/2002 | Embleton et al. |
| 6,428,487 B1 | 8/2002 | Burdorff et al. |
| 6,443,910 B1 | 9/2002 | Krueger et al. |
| 6,458,117 B1 | 10/2002 | Pollins |
| 6,468,248 B1 | 10/2002 | Gibbs |
| 6,478,751 B1 | 11/2002 | Krueger et al. |
| 6,488,636 B2 | 12/2002 | Bryan et al. |
| 6,523,698 B1 | 2/2003 | Dennehey et al. |
| 6,527,736 B1 | 3/2003 | Attinoer et al. |
| 6,527,778 B2 | 3/2003 | Athanasiou et al. |
| 6,540,694 B1 | 4/2003 | Van Bladel et al. |
| 6,540,697 B2 | 4/2003 | Chen |

(56) References Cited

U.S. PATENT DOCUMENTS

| | | |
|---|---|---|
| 6,547,511 B1 | 4/2003 | Adams |
| 6,547,561 B2 | 4/2003 | Meller et al. |
| 6,550,786 B2 | 4/2003 | Gifford et al. |
| 6,554,779 B2 | 4/2003 | Viola et al. |
| 6,555,212 B2 | 4/2003 | Boiocchi et al. |
| 6,572,563 B2 | 6/2003 | Ouchi |
| 6,575,745 B2 | 6/2003 | Meller et al. |
| 6,575,919 B1 | 6/2003 | Reiley et al. |
| 6,582,399 B1 | 6/2003 | Smith et al. |
| 6,585,622 B1 | 7/2003 | Shum et al. |
| 6,595,911 B2 | 7/2003 | LoVuolo |
| 6,595,979 B1 | 7/2003 | Epstein et al. |
| 6,613,054 B2 | 9/2003 | Scribner et al. |
| 6,616,632 B2 | 9/2003 | Sharp et al. |
| 6,620,111 B2 | 9/2003 | Stehens et al. |
| 6,626,848 B2 | 9/2003 | Nueenfeldt |
| 6,626,887 B1 | 9/2003 | Wu |
| 6,638,235 B2 | 10/2003 | Miller et al. |
| 6,656,133 B2 | 12/2003 | Voegele et al. |
| 6,689,072 B2 | 2/2004 | Kaplan et al. |
| 6,702,760 B2 | 3/2004 | Krause et al. |
| 6,702,761 B1 | 3/2004 | Damadian et al. |
| 6,706,016 B2 | 3/2004 | Cory et al. |
| 6,716,192 B1 | 4/2004 | Orosz, Jr. |
| 6,716,215 B1 | 4/2004 | David et al. |
| 6,716,216 B1 | 4/2004 | Boucher et al. |
| 6,730,043 B2 | 5/2004 | Krueger et al. |
| 6,730,044 B2 | 5/2004 | Stephens et al. |
| 6,749,576 B2 | 6/2004 | Bauer |
| 6,752,768 B2 | 6/2004 | Burdorff et al. |
| 6,752,816 B2 | 6/2004 | Culp et al. |
| 6,758,824 B1 | 7/2004 | Miller et al. |
| 6,761,726 B1 | 7/2004 | Findlay et al. |
| 6,796,957 B2 | 9/2004 | Carpenter et al. |
| 6,839,789 B2 | 1/2005 | Lehwalder et al. |
| 6,846,314 B2 | 1/2005 | Shapira |
| 6,849,051 B2 | 2/2005 | Sramek et al. |
| 6,855,148 B2 | 2/2005 | Foley et al. |
| 6,860,860 B2 | 3/2005 | Viola |
| 6,871,759 B2 | 3/2005 | Rake et al. |
| 6,875,183 B2 | 4/2005 | Cervi |
| 6,875,219 B2 | 4/2005 | Arramon et al. |
| 6,884,245 B2 | 4/2005 | Spranza |
| 6,887,209 B2 | 5/2005 | Kadziauskas et al. |
| 6,890,308 B2 | 5/2005 | Islam |
| 6,905,466 B2 | 6/2005 | Gibbs |
| 6,930,461 B2 | 8/2005 | Ruthowski |
| 6,942,669 B2 | 9/2005 | Kurc |
| 6,969,373 B2 | 11/2005 | Schwartz et al. |
| 7,001,342 B2 | 2/2006 | Faciszewski |
| 7,008,381 B2 | 3/2006 | Janssens |
| 7,008,383 B1 | 3/2006 | Damadian et al. |
| 7,008,394 B2 | 3/2006 | Geise et al. |
| 7,018,343 B2 | 3/2006 | Plishka |
| 7,025,732 B2 | 4/2006 | Thompson et al. |
| 7,063,672 B2 | 6/2006 | Schramm |
| 7,081,123 B2 | 7/2006 | Merboth et al. |
| 7,137,985 B2 | 11/2006 | Jahng |
| 7,186,257 B2 | 3/2007 | Kim |
| 7,207,949 B2 | 4/2007 | Miles et al. |
| 7,226,450 B2 | 6/2007 | Athanasiou et al. |
| 7,229,401 B2 | 6/2007 | Kindlein |
| 7,278,972 B2 | 10/2007 | Lamoureux et al. |
| 7,331,930 B2 | 2/2008 | Faciszewski |
| 7,565,935 B1 | 7/2009 | Phillips |
| 7,670,328 B2 | 3/2010 | Miller |
| 7,699,850 B2 | 4/2010 | Miller |
| 7,811,260 B2 | 10/2010 | Miller et al. |
| 7,815,642 B2 | 10/2010 | Miller |
| 7,850,620 B2 | 12/2010 | Miller et al. |
| 7,951,089 B2 | 5/2011 | Miller |
| 7,988,643 B2 | 8/2011 | Hoffmann et al. |
| 8,038,664 B2 | 10/2011 | Miller et al. |
| 8,142,365 B2 | 3/2012 | Miller |
| 8,217,561 B2 | 7/2012 | Fukuzawa et al. |
| 8,308,693 B2 | 11/2012 | Miller et al. |
| 8,419,683 B2 | 4/2013 | Miller et al. |
| 8,480,632 B2 | 7/2013 | Miller et al. |
| 8,506,568 B2 | 8/2013 | Miller |
| 8,641,715 B2 | 2/2014 | Miller |
| 8,656,929 B2 | 2/2014 | Miller et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,812,101 B2 | 8/2014 | Miller et al. |
| 8,870,872 B2 | 10/2014 | Miller |
| 8,876,826 B2 | 11/2014 | Miller |
| 8,944,069 B2 | 2/2015 | Miller et al. |
| 8,974,410 B2 | 3/2015 | Miller et al. |
| 8,998,348 B2 | 4/2015 | Miller et al. |
| 9,072,543 B2 | 7/2015 | Miller et al. |
| 9,078,637 B2 | 7/2015 | Miller |
| 9,295,487 B2 | 3/2016 | Miller et al. |
| 9,717,847 B2 | 8/2017 | Miller et al. |
| 2001/0005778 A1 | 6/2001 | Ouchi |
| 2001/0014439 A1 | 8/2001 | Meller et al. |
| 2001/0026051 A1 | 10/2001 | Gifford et al. |
| 2001/0047183 A1 | 11/2001 | Privitera et al. |
| 2001/0053888 A1* | 12/2001 | Athanasiou ........ A61B 10/0233 604/154 |
| 2002/0042581 A1 | 4/2002 | Cervi |
| 2002/0055713 A1 | 5/2002 | Gibbs |
| 2002/0120212 A1 | 8/2002 | Ritchart et al. |
| 2002/0133148 A1 | 9/2002 | Daniel et al. |
| 2002/0138021 A1 | 9/2002 | Pflueger |
| 2002/0143269 A1 | 10/2002 | Neuenfeldt |
| 2002/0151821 A1 | 10/2002 | Castellacci |
| 2002/0151902 A1 | 10/2002 | Riedel et al. |
| 2002/0158102 A1 | 10/2002 | Patton et al. |
| 2003/0028146 A1 | 2/2003 | Aves |
| 2003/0032939 A1 | 2/2003 | Gibbs |
| 2003/0036747 A1 | 2/2003 | Ie et al. |
| 2003/0050574 A1 | 3/2003 | Krueger |
| 2003/0078586 A1 | 4/2003 | Shapira |
| 2003/0114858 A1 | 6/2003 | Athanasiou et al. |
| 2003/0125639 A1 | 7/2003 | Fisher et al. |
| 2003/0153842 A1 | 8/2003 | Lamoureux et al. |
| 2003/0191414 A1 | 10/2003 | Reiley et al. |
| 2003/0195436 A1 | 10/2003 | Van Bladel et al. |
| 2003/0195524 A1 | 10/2003 | Barner |
| 2003/0199787 A1 | 10/2003 | Schwindt |
| 2003/0199879 A1 | 10/2003 | Spranza |
| 2003/0216667 A1 | 11/2003 | Viola |
| 2003/0225344 A1 | 12/2003 | Miller |
| 2003/0225364 A1 | 12/2003 | Kraft et al. |
| 2003/0225411 A1 | 12/2003 | Miller |
| 2004/0019297 A1 | 1/2004 | Angel |
| 2004/0019299 A1 | 1/2004 | Ritchart et al. |
| 2004/0034280 A1 | 2/2004 | Privitera et al. |
| 2004/0049128 A1 | 3/2004 | Miller et al. |
| 2004/0064136 A1 | 4/2004 | Papineau et al. |
| 2004/0073139 A1 | 4/2004 | Hirsch et al. |
| 2004/0092946 A1 | 5/2004 | Bagga et al. |
| 2004/0127814 A1 | 7/2004 | Negroni |
| 2004/0153003 A1 | 8/2004 | Cicenas et al. |
| 2004/0158172 A1 | 8/2004 | Hancock |
| 2004/0158173 A1 | 8/2004 | Voegele et al. |
| 2004/0162505 A1 | 8/2004 | Kaplan et al. |
| 2004/0191897 A1 | 9/2004 | Muschler |
| 2004/0210161 A1 | 10/2004 | Burdorff et al. |
| 2004/0210198 A1 | 10/2004 | Shih |
| 2004/0215102 A1 | 10/2004 | Ikehara et al. |
| 2004/0220497 A1 | 11/2004 | Findlay et al. |
| 2004/0249389 A1 | 12/2004 | Kim |
| 2005/0027210 A1 | 2/2005 | Miller |
| 2005/0040060 A1 | 2/2005 | Anderson et al. |
| 2005/0075581 A1 | 4/2005 | Schwindt |
| 2005/0085838 A1 | 4/2005 | Thompson et al. |
| 2005/0101880 A1 | 5/2005 | Cicenas et al. |
| 2005/0113716 A1 | 5/2005 | Mueller, Jr. et al. |
| 2005/0119660 A1 | 6/2005 | Bourlion et al. |
| 2005/0124915 A1 | 6/2005 | Eggers et al. |
| 2005/0131345 A1 | 6/2005 | Miller |

(56) References Cited

U.S. PATENT DOCUMENTS

| | | |
|---|---|---|
| 2005/0148940 A1 | 7/2005 | Miller |
| 2005/0165328 A1 | 7/2005 | Heske et al. |
| 2005/0165403 A1 | 7/2005 | Miller |
| 2005/0165404 A1 | 7/2005 | Miller |
| 2005/0171504 A1 | 8/2005 | Miller |
| 2005/0182394 A1 | 8/2005 | Spero et al. |
| 2005/0200087 A1 | 9/2005 | Vasudeva et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0228309 A1 | 10/2005 | Fisher et al. |
| 2005/0261693 A1 | 11/2005 | Miller et al. |
| 2006/0011506 A1 | 1/2006 | Riley |
| 2006/0015066 A1 | 1/2006 | Turieo et al. |
| 2006/0036212 A1 | 2/2006 | Miller |
| 2006/0052790 A1 | 3/2006 | Miller |
| 2006/0074345 A1 | 4/2006 | Hibner |
| 2006/0079774 A1 | 4/2006 | Anderson |
| 2006/0089565 A1 | 4/2006 | Schramm |
| 2006/0122535 A1 | 6/2006 | Daum |
| 2006/0129082 A1 | 6/2006 | Rozga |
| 2006/0144548 A1 | 7/2006 | Beckman et al. |
| 2006/0149163 A1 | 7/2006 | Hibner et al. |
| 2006/0167377 A1 | 7/2006 | Richart et al. |
| 2006/0167378 A1 | 7/2006 | Miller |
| 2006/0167379 A1 | 7/2006 | Miller |
| 2006/0189940 A1 | 8/2006 | Kirsch |
| 2006/0206132 A1 | 9/2006 | Conquergood et al. |
| 2007/0016100 A1 | 1/2007 | Miller |
| 2007/0149920 A1 | 6/2007 | Michels et al. |
| 2007/0213735 A1 | 9/2007 | Sandat et al. |
| 2007/0270775 A1 | 11/2007 | Miller et al. |
| 2008/0015467 A1 | 1/2008 | Miller |
| 2008/0015468 A1 | 1/2008 | Miller |
| 2008/0045857 A1 | 2/2008 | Miller et al. |
| 2008/0045860 A1 | 2/2008 | Miller et al. |
| 2008/0045861 A1 | 2/2008 | Miller et al. |
| 2008/0045965 A1 | 2/2008 | Miller et al. |
| 2008/0140014 A1 | 6/2008 | Miller et al. |
| 2008/0177200 A1 | 7/2008 | Ikehara et al. |
| 2008/0215056 A1 | 9/2008 | Miller et al. |
| 2008/0221580 A1 | 9/2008 | Miller et al. |
| 2009/0069716 A1 | 3/2009 | Freeman et al. |
| 2009/0093677 A1 | 4/2009 | Smith |
| 2009/0248029 A1 | 10/2009 | Paulos |
| 2010/0204611 A1 | 8/2010 | Zambelli |
| 2010/0298784 A1 | 11/2010 | Miller |
| 2011/0046507 A1 | 2/2011 | Herndon |
| 2011/0082387 A1 | 4/2011 | Miller et al. |
| 2011/0184425 A1 | 7/2011 | Cheraux |
| 2011/0203821 A1 | 8/2011 | Puzio et al. |
| 2011/0251518 A1 | 10/2011 | Swisher et al. |
| 2011/0306841 A1 | 12/2011 | Lozman et al. |
| 2012/0165832 A1 | 6/2012 | Oostman et al. |
| 2015/0129456 A1 | 5/2015 | Miller et al. |
| 2015/0223786 A1 | 8/2015 | Morgan et al. |

FOREIGN PATENT DOCUMENTS

| | | |
|---|---|---|
| CN | 2664675 | 12/2004 |
| CN | 2320209 | 5/2009 |
| DE | 10057931 A1 | 11/2000 |
| EP | 517000 | 12/1992 |
| EP | 0807412 | 11/1997 |
| EP | 1099450 | 5/2001 |
| EP | 1314452 | 5/2003 |
| EP | 1447050 | 8/2004 |
| EP | 1421907 | 10/2010 |
| FR | 853349 | 3/1940 |
| FR | 2457105 | 5/1979 |
| FR | 2516386 | 11/1981 |
| GB | 629 824 A | 9/1949 |
| GB | 2130890 | 6/1984 |
| JP | 59119808 | 8/1984 |
| JP | 6132663 | 9/1986 |
| JP | 1052433 | 2/1989 |
| JP | 2001505076 | 4/2001 |
| WO | 9208410 | 5/1992 |
| WO | 9307819 | 4/1993 |
| WO | 9325151 | 12/1993 |
| WO | 9631164 | 10/1996 |
| WO | 9806337 | 2/1998 |
| WO | 9852638 | 11/1998 |
| WO | 99/18866 | 4/1999 |
| WO | 9952444 | 10/1999 |
| WO | 0009024 | 2/2000 |
| WO | 00/56220 | 9/2000 |
| WO | 2001/78590 | 10/2001 |
| WO | 0193931 | 12/2001 |
| WO | 0241792 | 5/2002 |
| WO | 02096497 | 12/2002 |
| WO | 03015637 | 2/2003 |
| WO | 2005072625 | 8/2005 |
| WO | 2005110259 | 11/2005 |
| WO | 2005112800 | 12/2005 |
| WO | 2008033874 | 3/2008 |
| WO | 2008081438 | 7/2008 |
| WO | 2009070896 | 6/2009 |
| WO | 2011070593 | 6/2011 |
| WO | 2011123703 | 10/2011 |
| WO | 2012175946 | 12/2012 |

OTHER PUBLICATIONS

International Preliminary Report on Patentability, PCT/US2007/072217, 11 pages, dated Feb. 12, 2009.
Official Action for European Application No. 03756317.8 (4 pages), dated Dec. 28, 2006.
Invitation to Pay Additional Fees for Application No. PCT/US2006/025201 (6 pages), dated Oct. 26, 2006.
Australian Exam Report on Patent Application No. 2003240970, 2 pages, dated Oct. 15, 2007.
International Search Report and Written Opinion for International Application No. PCT/US2006/025201 (18 pages), dated Jan. 29, 2007.
International Search Report, PCT/US2007/072209, 9 pages, dated Mar. 12, 2007.
International Search Report, PCT/US2007/072217, 9 pages, dated Mar. 12, 2007.
Preliminary Report on Patentability, PCT/US2006/025201, 12 pages, dated Feb. 7, 2008.
Gunal et al., Compartment Syndrome After Intraosseous Infusion: An Experimental Study in Dogs, Journal od Pediatric Surgery, vol. 31, No. 11, pp. 1491-1493, Nov. 1996.
International Search Report, PCT/US2007/072217, 20 pages dated Mar. 31, 2008.
International Search Report, PCT/US2007/072209, 18 pages, dated Apr. 25, 2008.
Communication Pursuant to Article 94(3) EPC, Application No. 05 712 091.7-1265, 4 pages, dated Apr. 8, 2008.
Notification of the Chinese Office Action, Application No. 200580003261.81, 3 pages, dated Mar. 1, 2008.
International Search Report and Written Opinion, PCT/US08/500346, 12 pages, dated May 22, 2008.
Chinese Office Action, Application No. 2005800003261, (with English translation), (9 pgs), dated Jan. 16, 2009.
Japanese Office Action, Application No. 2004-508,670, (with English summary), (13 pages), dated Apr. 21, 2009.
PCT Preliminary Report on Patentability, PCT/US/2008/050346, (8 pgs), dated Jul. 23, 2009.
European Office Action and Search Report, Application No. 09150973.7, 8 pages, dated Oct. 23, 2009.
International Preliminary Report on Patentability, PCT/US08/52943, 7 pages, dated Oct. 15, 2009.
Japanese Office Action, Application No. 2004-508,669, (with English summary), (9 pages), dated Aug. 3, 2009.
Chinese Office Action, Application No. 200780000590.6, (with English translation), (13 pages), dated Aug. 21, 2009.

(56) References Cited

OTHER PUBLICATIONS

International Preliminary Report on Patentability PCT/US2005/002484, 9 pages, dated Aug. 3, 2006.
International PCT Search Report and Written Opinion PCT/US2004/037753, 16 pages, dated Jul. 8, 2005.
International PCT Search Report and Written Opinion PCT/US2005/002484, 15 pages, dated Jul. 22, 2005.
International Preliminary Report on Patentability, PCT/US/2007/078203, 13 pages, dated Mar. 26, 2009.
International Preliminary Report on Patentability, PCT/US/2007/078207, 10 pages, dated Mar. 26, 2009.
International Preliminary Report on Patentability, PCT/US/2007/078205, 10 pages, dated Mar. 26, 2009.
International Preliminary Report on Patentability, PCT/US/2007/078204, 11 pages, dated Apr. 2, 2009.
Vidacare Corporation Comments to Intraosseous Vascular Access Position Paper, Infusion Nurses Society, 6 pages, May 4, 2009.
International Preliminary Report on Patentability, PCT/US/2007/072209, 10 pages, dated May 14, 2009.
Communication relating to the results of the partial International Search Report for PCT/US2005/002484, 6 pages, dated May 19, 2005.
Richard 0. Cummings et al., "ACLS—Principles and Practice", ACLS—The Reference Textbook, American Heart Association, pp. 214-218, 2003.
International PCT Search Report, PCT/US03/17167, 8 Pages, dated Sep. 16, 2003.
International PCT Search Report, PCT/US03/17203, 8 Pages, dated Sep. 16, 2003.
International PCT Search Report PCT/US2004/037753, 6 Pages, dated Apr. 19, 2005.
Astrom, K.G., "Automatic Biopsy Instruments Used Through a Coaxial Bone Biopsy System with an Eccentric Drill Tip," Acta Radiologica, 1995; 36:237-242, May 1995.
Astrom, K. Gunnar 0., "CT-guided Transsternal Core Biopsy of Anterior Mediastinal Masses," Radiology 1996; 199:564-567, May 1996.
international PCT Search Report PCT/US03/17167, 3 pages, dated Sep. 16, 2003.
Communication relating to the results of the partial International Search Report for Mailed PCT/US2005/002484, 6 pages, dated May 19, 2005.
Cummins, Richard O., et al, "ACLS—Principles and Practice", ACLS—The Reference Textbook, American Heart Association, pp. 214-218, 2003.
Riley et al., "A Pathologist's Perspective on Bone Marrow Aspiration Biopsy: I. Performing a Bone Marrow Examination," Journal of Clinical Laboratory Analysis 18, pp. 70-90, 2004.
Pediatrics, Official Journal of the American Academy of Pediatrics, Pediatrics; 2005, American Heart Association Guidelines for Cardiopulmonary Resuscitation and Emergency Cardiovascular Care of Pediatric and Neonatal Patients: Pediatric Advanced Life Support, Downloaded from www.pediatrics.org.
Liakat A. Parapia, Trepanning or trephines: a history of bone marrow biopsy, British Journal of Haematology, Haematology, pp. 14-19 2007.
Pediatric Emergency, Intraosseous Infusion for Administration of Fluids and Drugs, www.cookgroup.com, 1 pg, 2000.
Michael Trotty, "Technology (A Special Report)—The Wall Street Journal 2008 Technology Innovation Awards—This years winners include: an IV alternative, a better way to make solar panels, a cheap, fuel efficient car and a better way toto see in the dark", The Wall Street Journal, Factiva, 5 pages, 2008.
Buckley et al., CT-guided bone biopsy: Initial experience with commercially available hand held Black and Decker drill, European Journal of Radiology 61, pp. 176-180, 2007.
Hakan et al., CT-guided Bone BiopsyPerformed by Means of Coaxial Bopsy System with an Eccentric Drill, Radiology, pp. 549-552, Aug. 1993.
European Search Report 08158699.2-1265, 4 pages, Aug. 2008.
International Search Report and Written Opinion, PCT/US2007/078204, 14 pages, dated May 15, 2008.
International Search Report and Written Opinion, PCT/US08/52943, 8 pages, dated Sep. 26, 2008.
European Office Action Communication, Application No. 08158699.2-1265/1967142, 10 pages, dated Nov. 4, 2008.
PCT Invitation to Pay Additional Fees, PCT/US2007/072209, 9 pages, dated Dec. 3, 2007.
"Proven reliability for quality bone marrow samples", Special Procedures, Cardinal Health, 6 pages, 2003.
F.A.S.T. 1 Intraosseous Infusion System with Depth-Control Mechanism Brochure, 6 pages, 2000.
BioAccess.corn, Sino le Use Small Bone Power Tool—How It Works, 1 Pg., Jun. 9, 2008.
International Search Report and Written Opinion, PCT/US2007/078203, 15 pages, dated May 13, 2008.
International Search Report and Written Opinion, PCT/US2007/072202, 17 pages, dated Mar. 25, 2008.
International Search Report and Written Opinion, PCT/US2007/078207, 13 pages, dated Apr. 7, 2008.
International Search Report and Written Opinion, PCT/US2007/078205, 13 pages, dated Sep. 11, 2007.
European Office Action EP03731475.4, 4 pages, dated Oct. 11, 2007.
Chinese Office Action w/english translation; Application No. 200680021872.X; pp. 8, dated Nov. 6, 2009.
Chinese Office Action with English translation; Application No. 200910006631.3; pp. 12, dated Mar. 11, 2010.
European Extended Search Report, Application No. EP10153350.3, 5 pages, dated Mar. 11, 2010.
European Extended Search Report, Application No. EP08021732.6, 7 pages, dated Nov. 13, 2009.
European Office Action; Application No. 09 155 111.9-2310; pp. 3, dated Nov. 25, 2009.
Chinese Office Action with English translation; Application No. 200380000022.0; pp. 10; dated Dec. 13, 2010.
Chinese Office Action with English translation; Application No. 200880000022.0; pp. dated Sep. 22, 2011.
Chinese Office Action with English translation; Application No. 200830000022.0; pp. dated May 25, 2012.
Chinese Office Action with English translation; Application No. 200730000585.5, pp. 15.
European Office Action dated Jan. 19, 2011 and Response dated Jul. 21, 2011 , EP Application No. 09150973.7.
European Office Action dated Dec. 22, 2011 and Response dated Jun. 29, 2012, EP Application No. 09150973.7.
European Office Action dated Feb. 21, 2007 and Response dated Jun. 27, 2007, EP Application No. 05712091.7.
European Office Action dated Apr. 3, 2008 and Response dated May 15, 2008, EP Application No. 05712091.7.
European Office Action dated Sep. 21, 2007 and Response dated Nov. 26, 2007, EP Application No. 05712091.7.
European Office Action dated Sep. 3, 2010 and Response dated Mar. 17, 2011 , EP Application No. 10153350.3.
European Telephone Consultation Report dated Apr. 21, 2009 and Response dated Jun. 24, 2009, EP Aoolication No. 08158699.2.
European Telephone Consultation Report dated Sep. 23, 2009 and Response dated Oct. 28, 2009 , EP Application No. 08158699.2.
International Search Report and Written Opinion for international application PCT/US2008/0500346. dated May 22, 2008.
Interview Summary for U.S. Appl. No. 11/190,331. dated Jul. 13, 2009.
Office Action for Japanese Application No. 2004-508,670 with English Translation, dated Aug. 31, 2010.
Notice of Allowance in U.S. Appl. No. 11/042,912, dated Sep. 24, 2013.
Notice of Allowance in U.S. Appl. No. 11/380,340 dated Aug. 22, 2014.
Notice of Allowance in U.S. Appl. No. 11/619,390 dated Nov. 6, 2014.
Notice of Allowance in U.S. Appl. No. 11/620,927 dated Jun. 3, 2014.

(56) References Cited

OTHER PUBLICATIONS

Notice of Allowance in U.S. Appl. No. 11/853,678 dated Jul. 11, 2013.
Notice of Allowance in U.S. Appl. No. 11/853,678, dated Oct. 11, 2013.
Notice of Allowance in U.S. Appl. No. 11/853,678, dated Nov. 8, 2013.
Notice of Allowance in U.S. Appl. No. 12/259,745 dated Nov. 7, 2014.
Notice of Allowance in U.S. Appl. No. 12/331,979, dated Dec. 23, 2013.
Notice of Allowance in U.S. Appl. No. 12/407,651 dated Jun. 11, 2014.
Notice of Allowance in U.S. Appl. No. 12/427,310, dated Nov. 29, 2013.
Notice of Allowance in U.S. Appl. No. 12/899,696 dated Jul. 18, 2013,.
Notice of Allowance in U.S. Appl. No. 12/899,696, Appl. Nov. 12, 2013.
Notice of Allowance in U.S. Appl. No. 14/721,144 dated Jul. 22, 2014.
Notice of Allowance issued in U.S. Appl. No. 11/253,467, dated Mar. 29, 2013.
Notice of Allowance issued in U.S. Appl. No. 11/253,959, dated May 20, 2013.
Notice of Allowance dated Mar. 4, 2014 in U.S. Appl. No. 11/253,467.
Office Action for Canadian application 2,612,483, dated Dec. 27, 2013.
Office Action for Chinese application 200880000182.5 (English translation). dated Sep. 10, 2010.
Office Action Action for for Chinese application 200380000182.5 (English translation) dated Jun. 27, 2013.
Office Action for Chinese application 200880000182.5 with English translation. dated Jun. 27, 2013.
Office Action for Chinese application 200910006631.3 (English translation). dated Nov. 11, 2010.
Office Action for Chinese application 200910006631.3. dated Mar. 22, 2011.
Office Action for for Chinese application 201210169456.0 with English translation. dated Aug. 28, 2013.
Office Action for Chinese application 201210169546.0 with English translation. dated Apr. 18, 2014.
Office Action for European application 05712091.7. dated Sep. 21, 2007.
Office Action for European application 08021732.6. dated Oct. 2, 2013.
Office Action for European application 08799753.2 dated Sep. 29, 2014.
Office Action for European Application 09150973.7-1269 dated Dec. 22, 2011.
Office Action for European application 10153350.3. dated Sep. 8, 2010.
Office Action for Taiwanese application 093134480 (English Translation). dated Feb. 11, 2011.
Office Action for Taiwanese application 94102179 (English translation). dated May 13, 2010.
Office Action for U.S. Appl. No. 10/449,476. dated Oct. 29, 2008.
Office Action for U.S. Appl. 10/449,476. dated May 29, 2009.
Office Action for U.S. Appl. No. 10/449,503. dated Apr. 1, 2009.
Office Action for U.S. Appl. No. 11/042,912. dated Jul. 23, 2009.
Office Action for U.S. Appl. No. 11/042,912. dated Mar. 19, 2010.
Office Action for U.S. Appl. No. 11/042,912. dated Nov. 28, 2008.
Office Action for U.S. Appl. No. 11/064,156. dated Jun. 19, 2009.
Office Action for U.S. Appl. No. 11/190,331. dated Mar. 23, 2009.
Office Action for U.S. Appl. No. 11/253,467. dated Apr. 28, 2011.
Office Action for U.S. Appl. No. 11/253,467. dated Jul. 22, 2010.
Office Action for U.S. Appl. No. 11/253,467. dated Oct. 29, 2010.
Office Action for U.S. Appl. No. 11/253,959. dated Aug. 5, 2010.
Office Action for U.S. Appl. No. 11/253,959. dated Mar. 30, 2011.
Office Action for U.S. Appl. No. 11/253,959. dated Oct. 18, 2010.
Office Action for U.S. Appl. No. 11/427,501. dated Aug. 7, 2008.
Office Action for U.S. Appl. No. 11/427,501. dated May 13, 2009.
Office Action for U.S. Appl. No. 11/427,501. dated Oct. 21, 2009.
Office Action for U.S. Appl. No. 11/853,685. dated Jun. 24, 2009.
Office Action for U.S. Appl. No. 12/259,745. dated Jul. 17, 2009.
Office Action for U.S. Appl. No. 12/905,659. dated Mar. 21, 2011.
Office Action for U.S. Appl. No. 12/905,659. dated May 13, 2011.
Office Action in Canadian Patent Application No. 2,612,433, dated Aug. 22, 2014.
Office Communication for European application 09150973.7-1269. dated Jan. 19, 2011.
Office Communication in European Application No. 08021732.6, dated Jul. 20, 2013.
Office Communication in European Application No. 10153350.3, dated Jun. 14, 2011.
Request for Continued Examination and Amendment for U.S. Appl. No. 11/731,568, filed Sep. 17, 2009.
Response to Extended European Search Report in European Application No. 10153350.3, filed Jun. 30, 2010.
Response to Interview Summary for U.S. Appl. No. 11/190,331 and Amendment. filed Aug. 12, 2009.
Response to Office Action for European application 10153350.3. Filed Mar. 17, 2011.
Response to Office Action for U.S. Appl. No. 10/449,476, filed Aug. 12, 2009.
Response to Office Action for U.S. Appl. No. 10/449,503, filed Jul. 1, 2009.
Response to Office Action for U.S. Appl. No. 11/190,331, filed Jun. 22, 2009.
Response to Office Action for U.S. Appl. No. 11/427,501, filed Jul. 1, 2009.
Response to Office Communication in European Application No. 10153350.3, filed Feb. 9, 2012.
Special Procedures, Cardinal Health, "Proven reliability for quality bone marrow samples," 2003.
European Search Report issued in European Patent Application No. 17198059.2 dated Jan. 29, 2018.

* cited by examiner

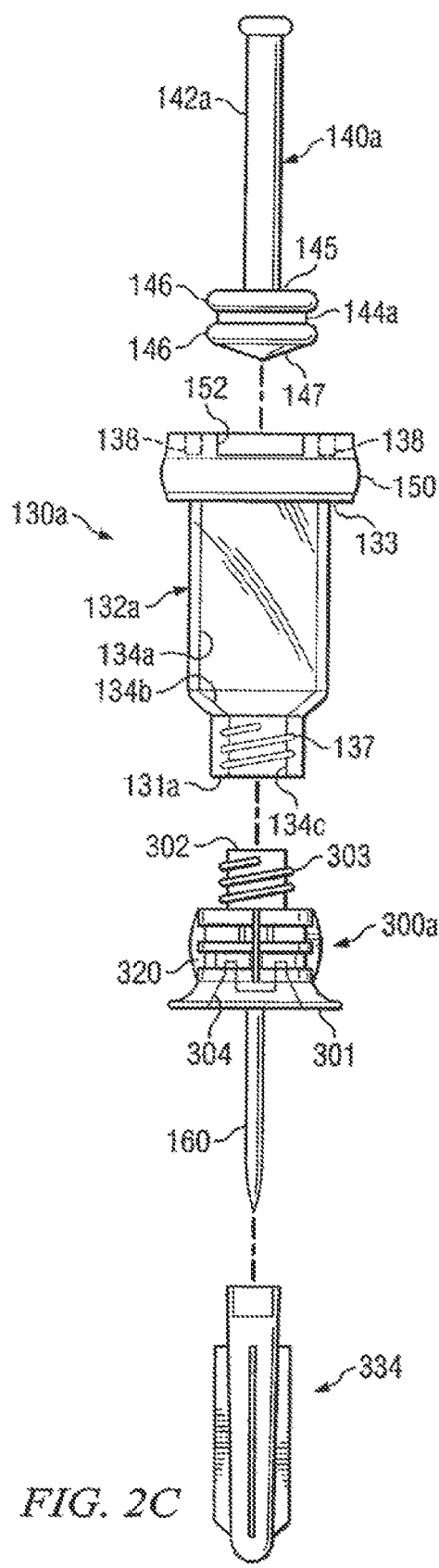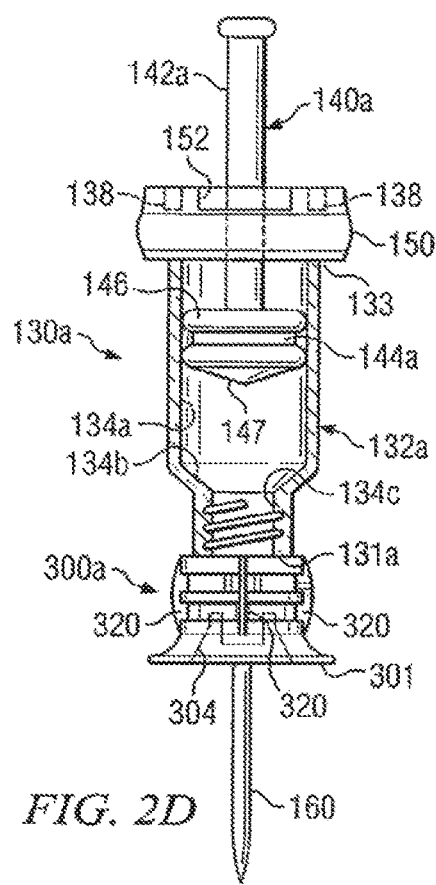
FIG. 2C
FIG. 2D

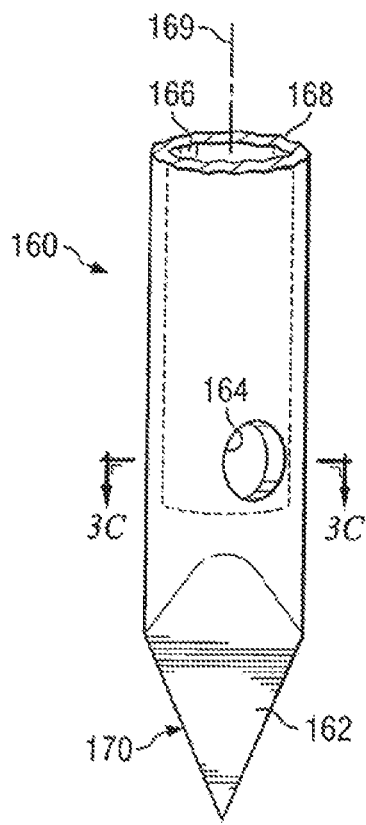
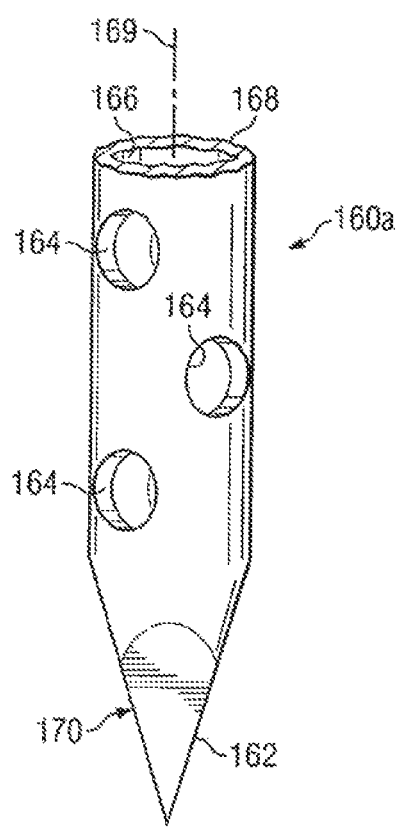
FIG. 3A  FIG. 3B
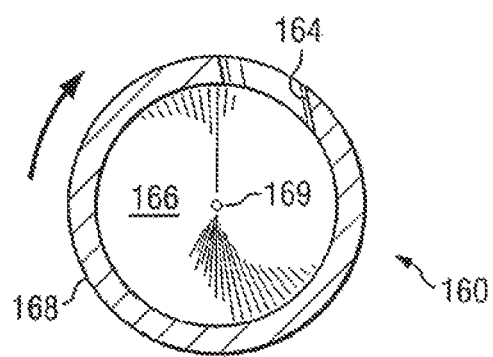
FIG. 3C

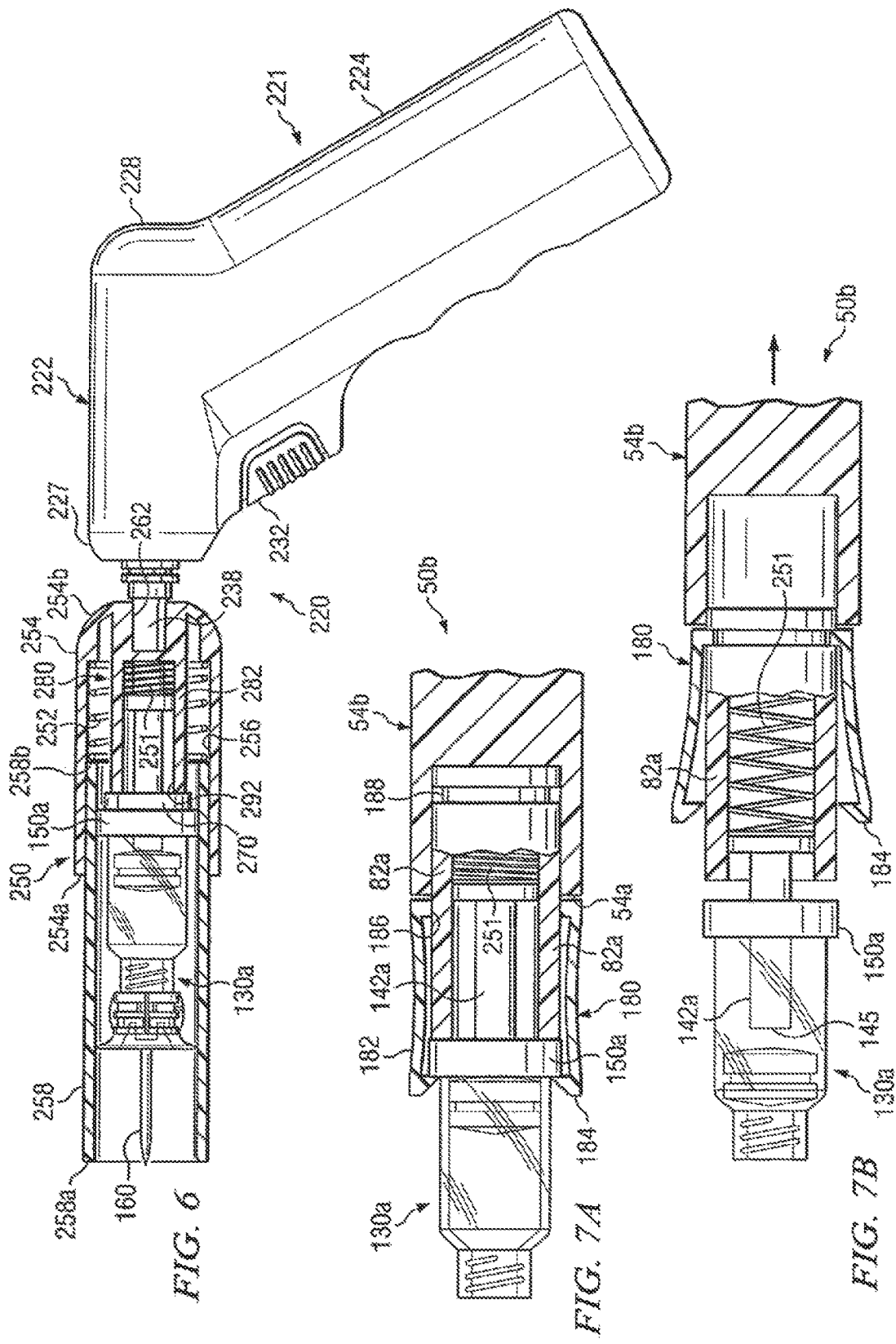

APPARATUS TO INJECT FLUIDS INTO BONE MARROW AND OTHER TARGET SITES

RELATED APPLICATION

This application is a continuation application of U.S. patent application Ser. No. 12/718,638, filed Mar. 5, 2010, which is a divisional application of U.S. patent application Ser. No. 12/347,506, filed Dec. 31, 2008, now U.S. Pat. No. 8,038,664, which is a divisional application of U.S. patent application Ser. No. 11/190,331, filed Jul. 27, 2005, now U.S. Pat. No. 7,811,260, which is a continuation-in-part application of U.S. patent application Ser. No. 10/449,503, filed May 30, 2003, now U.S. Pat. No. 7,670,328, which claims the benefit of U.S. Provisional Patent Application No. 60/384,756, filed May 31, 2002, the contents of which are hereby incorporated in their entirety by reference.

TECHNICAL FIELD

The present disclosure is related to apparatus and methods for delivery of fluids to a target site such as, but not limited to, bone marrow of a bone and removal of fluids from a target site.

BACKGROUND

Every year, millions of patients are treated for life threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications.

An essential element for treating all such emergencies is the rapid establishment of an intravenous (IV) line in order to administer drugs and fluids directly into the circulatory system. Whether in the ambulance by paramedics, or in the emergency room by emergency specialists, the goal is the same—to start an IV in order to administer life-saving drugs and fluids. To a large degree, the ability to successfully treat such critical emergencies is dependent on the skill and luck of the operator in accomplishing vascular access. While it is relatively easy to start an IV on some patients, doctors, nurses and paramedics often experience great difficulty establishing IV access in approximately 20 percent of patients. These patients are probed repeatedly with sharp needles in an attempt to solve this problem and may require an invasive procedure to finally establish an intravenous route.

A further complicating factor in achieving IV access occurs "in the field" e.g. at the scene of an accident or during ambulance transport where it is difficult to see the target and excessive motion make accessing the venous system very difficult.

In the case of patients with chronic disease or the elderly, the availability of easily-accessible veins may be depleted. Other patients may have no available IV sites due to anatomical scarcity of peripheral veins, obesity, extreme dehydration or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

SUMMARY

In accordance with teachings of the present disclosure, an apparatus operable to deliver a quantity of fluid to a target site such as bone marrow of a bone may be provided. The apparatus may include a driver, a plunger operating and cartridge drive mechanism and a cartridge assembly having a fluid reservoir with a bone penetrating needle coupled thereto.

In another embodiment an apparatus for delivering a quantity of medication to a target site may include a driver, a plunger operating assembly or a plunger barrel having a first spring, a retractable sleeve having a second spring and a fluid reservoir with a bone penetrator attached thereto.

In still another embodiment an apparatus for delivering a quantity of fluid to bone marrow of a bone is provided that may include a powered driver having a drill shaft operable for attachment with a plunger operating and cartridge drive mechanism, a gear assembly operable to engage and rotate the drill shaft, a motor, a power supply and associated circuitry operable to power the motor. The plunger operating and cartridge drive mechanism may include a plunger operating assembly and a retractable sleeve. A cartridge assembly having a fluid reservoir along with a plunger assembly and a bone penetrating needle may be releasably engaged with the plunger operating and cartridge drive mechanism.

In another embodiment a method for delivering a quantity of medication to a target site such as, but not limited to, bone marrow of a bone may be provided including compressing or cocking a portion of a plunger operating and cartridge drive mechanism, inserting a fluid filled cartridge assembly into the cocked plunger operating and cartridge drive mechanism and penetrating into bone marrow until the plunger operating and cartridge drive mechanism injects a quantity of fluid into the bone marrow.

In a further embodiment a cartridge assembly operable to deliver medication to bone marrow of a bone may be provided with a detachable fluid reservoir, a plunger assembly, a bone penetrating needle and associated fittings. The fluid reservoir may be formed at least in part from glass, glass composites, plastic or plastic composites.

For some embodiments, a bone penetrating needle may include a hollow longitudinal bore with a closed tip at one end of the longitudinal bore. Side ports communicating with the longitudinal bore of the bone penetrating needle may be angled to block or facilitate passage of certain substances.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 2C is a schematic, exploded drawing in elevation showing another example of a cartridge assembly satisfactory for use with an apparatus operable to deliver a quantity of medication to bone marrow;

FIG. 2D is a schematic drawing in elevation and in section showing the cartridge assembly of FIG. 2C;

FIG. 3A is a schematic drawing in elevation with portions broken away showing one example of a bone penetrating needle operable for communicating fluids with bone marrow;

FIG. 3B is a schematic drawing in elevation with portions broken away showing another example of a bone penetrating needle operable for communicating fluids with bone marrow;

FIG. 3C is a schematic drawing in section taken along lines 3C-3C of FIG. 3A;

FIG. 6 is a schematic drawing in section and in elevation showing another example of an apparatus including a driver operable to deliver a quantity of medication to bone marrow;

FIG. 7A is a schematic drawing in section and in elevation with portions broken away showing another example of a cartridge assembly releasably engaged with a plunger operating and cartridge drive mechanism incorporating accordance with teachings of the present disclosure;

FIG. 7B is a schematic drawing in section and in elevation with portions broken away showing release of the cartridge assembly of FIG. 7 A from the plunger operating and cartridge drive mechanism in accordance with teachings of the present disclosure;

DETAILED DESCRIPTION

Preferred embodiments of the disclosure and advantages are best understood by reference to FIGS. 1A-8B wherein like numbers refer to same and like parts.

The term "fluid" may be used within this patent application to include any liquid or any mixture of liquids, particulate matter, dissolved medication and/or drugs appropriate for injection into bone marrow or other target sites. The term "fluid" may also be used within this patent application to include body fluids such as, but not limited to, blood and cells which may be withdrawn from a target site.

The terms "fluid reservoir" and "reservoir" may be used in this patent application to include any chamber, cavity, ampoule, barrel, receptacle or any other device satisfactory for use with a cartridge assembly or other apparatus incorporating teachings of the present disclosure.

Examples of apparatus operable to access bone marrow and other target sites in accordance with teachings of the present disclosure are shown generally in FIGS. 1A-4B and 6-8B. One example of a method to access bone marrow or other target sites in accordance with teachings of the present disclosure is shown generally in FIG. 5. However, the present disclosure is not limited to examples such as shown in FIGS. 1A-4B and 6-8B or the method of delivering fluid to bone marrow as outlined in FIG. 5.

Figure 1A:
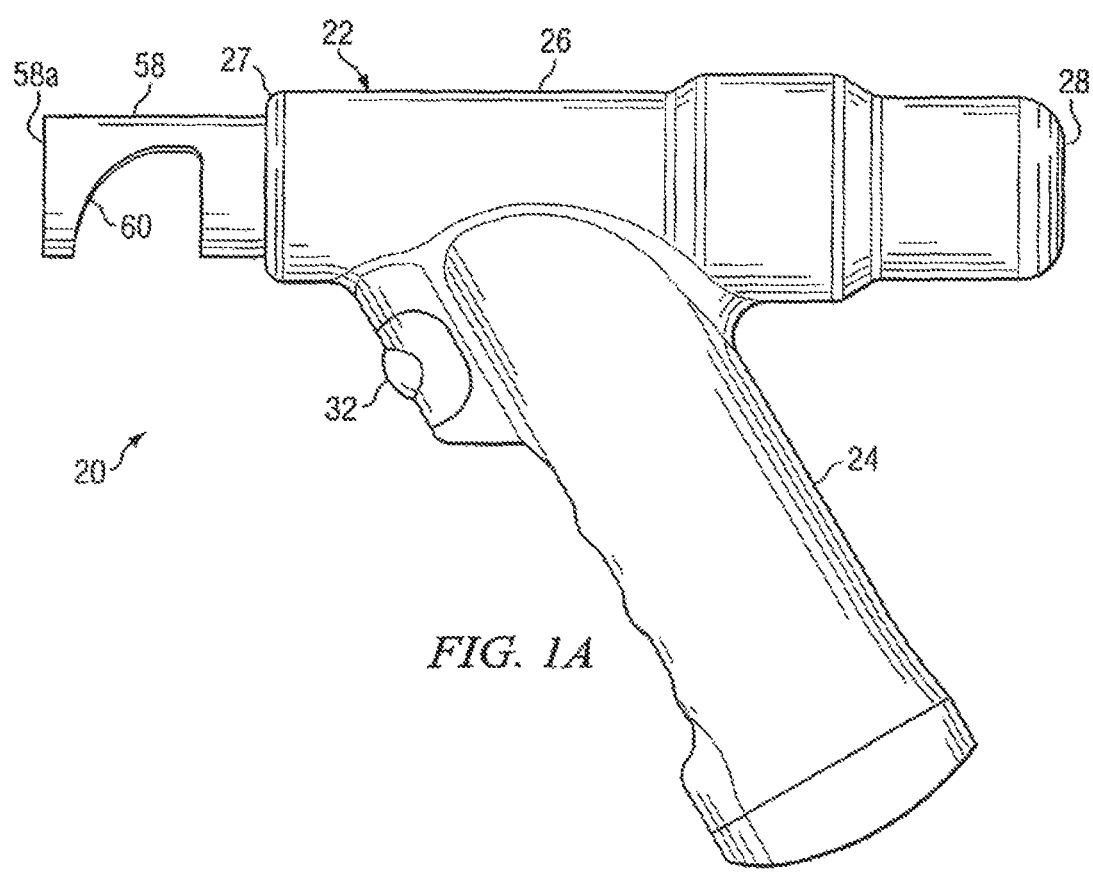
FIG. 1A is a schematic drawing in elevation showing one example of an apparatus operable to deliver a quantity of medication to bone marrow.
Figure 1B:
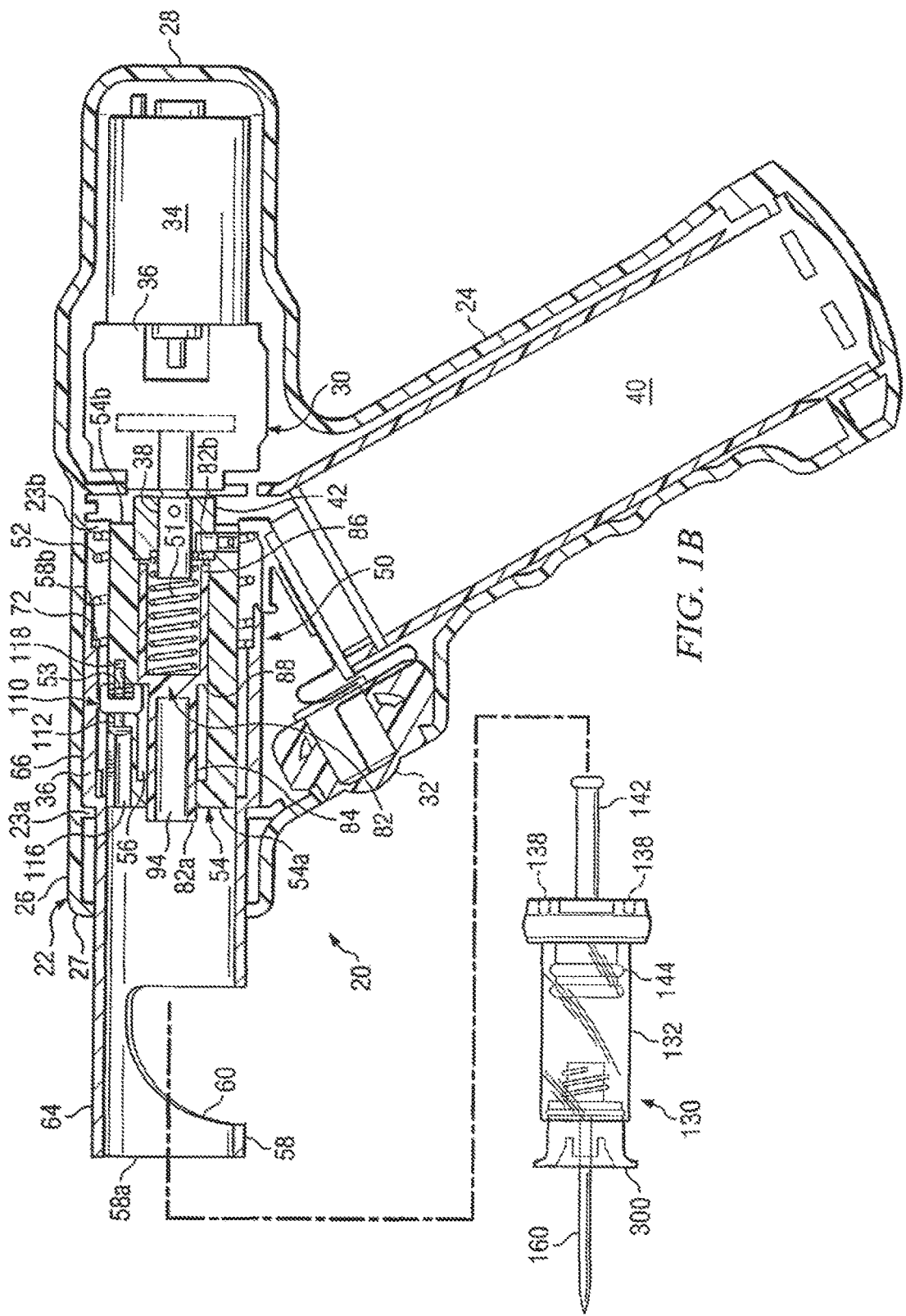
FIG. 1B is an exploded, schematic drawing in section and in elevation with portions broken away showing one example of an apparatus operable to deliver a quantity of medication to bone marrow in an unloaded, cocked position.
Figure 1C:
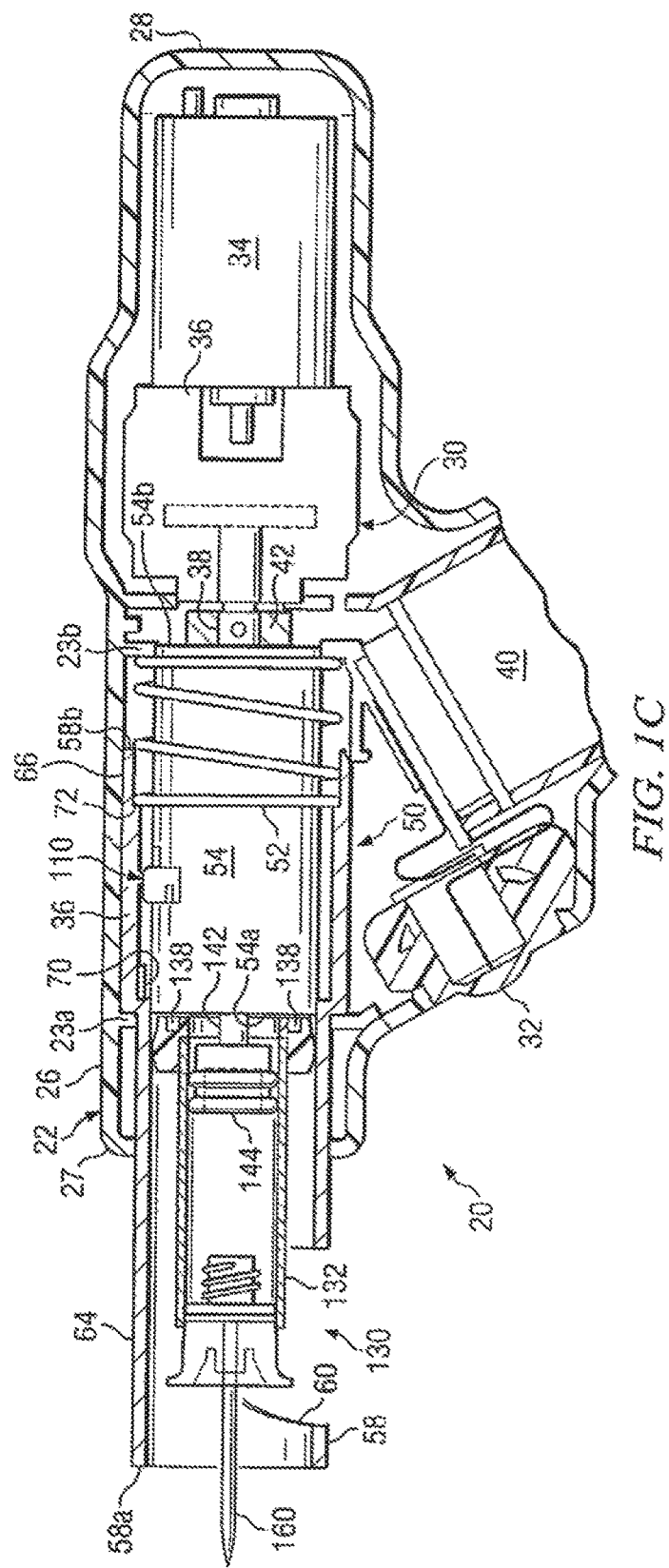
FIG. 1C is a schematic drawing in section with portions broken away showing one example of an apparatus operable to deliver a quantity of medication to bone marrow in a loaded position.
Figure 1D:
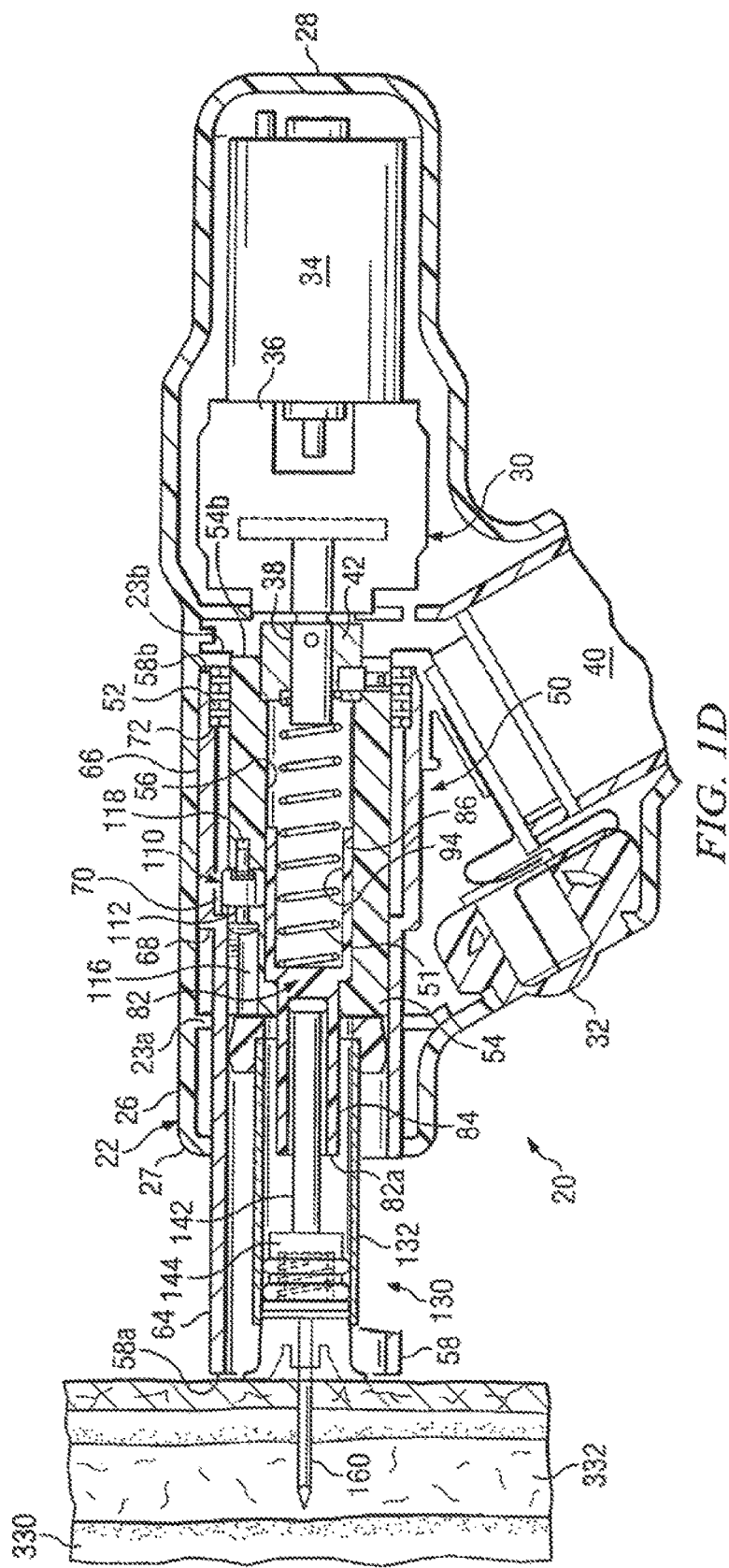
FIG. 1D is a schematic drawing in section with portions broken away showing one example of an apparatus operable to delivery a quantity of medication to bone marrow in a third, released position.

Various features of the present disclosure may be described with respect to apparatus 20 as shown in FIGS. 1A-1D and apparatus 220 as shown in FIG. 6. Apparatus 20 may have several positions such as an uncocked and unloaded position (not expressly shown), a cocked and unloaded position such as shown in FIG. 1B, a cocked and loaded position such as shown in FIG. 1C and a discharged position after fluid has been injected from a cartridge assembly at a target site such as shown in FIG. 1D.

Apparatus 20, as shown in FIGS. 1A-1D, may include housing 22 with driver assembly 30 and plunger operating and cartridge drive mechanism 50 disposed therein. Cartridge assembly 130 may be disposed within portions of housing 22. See FIGS. 1B, 1C and 1D. Housing 22 may include handle 24 which has been sized and contoured to fit the hand of an operator (not expressly shown). Handle 24 may include on/off switch or trigger 32. Housing 22 may also include receiver portion 26 having a generally hollow, tubular configuration. First end or distal end 27 of receiver portion 26 may be open with portions of retractable sleeve 58 slidably disposed therein. Second end or proximal end 28 of receiver portion 26 may be sealed or closed to protect various components associated with driver assembly 30 and plunger operating and cartridge drive mechanism 50.

Driver assembly 30 may include motor 34 connected to gearbox 36. Gearbox 36 may be attached to drive shaft 38 to produce rotational motion of plunger operating and cartridge drive mechanism 50. Various types of motors may be satisfactorily used to produce rotational, reciprocal or any other type of motion suitable to achieve results. In this example embodiment, motor 34 may be powered by battery pack 40. In alternative embodiments, motor 34 may be powered by electricity from a standard wall outlet, an AC to DC converter solar power generator. A compressed or wound spring, gas cartridge or any other satisfactory power source for operating a motor may also be used to operate apparatus 20.

Plunger operating and cartridge drive mechanism 50 may include first spring 51, second spring 52 and third spring 53. See FIGS. 1B, 1C and 1D. First spring 51 may sometimes be referred to as "plunger spring" 51. Second spring 52 may sometimes be referred to as "retractable sleeve spring" 52. Third spring 53 may sometimes be referred to as "torsional spring" or "pawl latch spring" 53. Various functions associated with springs 51, 52 and 53 will be discussed later in more detail.

Plunger operating and cartridge drive mechanism 50 may also include rotatable housing 54, retractable sleeve 58, plunger operating assembly 82, and pawl latch assembly 110. Retractable sleeve 58 may sometimes be referred to as "spring loaded retractable sleeve 58." Plunger operating assembly 82 may sometimes be referred to as "spring loaded plunger barrel 82." Pawl latch assembly 110 may sometimes be referred to as "spring loaded pawl latch assembly 110." Each of these components will be discussed later in more detail.

Drive housing 54 may be used to transmit rotational forces or drilling forces from drive shaft 38 to a cartridge assembly releasably engaged within plunger operating and cartridge drive mechanism 50. The cartridge assembly may include a fluid reservoir, a plunger assembly and a hollow, bone penetrating needle. Hollow, bone penetrating needles and hollow drill bits incorporating teachings of the present disclosure may sometimes be referred to as "bone penetrators." Rotational and/or drilling forces from drive shaft 38 may be used to insert a bone penetrating needle into bone marrow at a selected target site.

Examples of cartridge assemblies incorporating teachings of the present disclosure are shown in FIGS. 1B, 1D, 1C, 2A and 2B. However, a wide variety of other cartridge assemblies may be satisfactorily used with a plunger operating and cartridge drive mechanism incorporating teachings of the present disclosure. The present disclosure is not limited to cartridge assemblies 130 and 130a. The present disclosure is also not limited to using only rotational and/or drilling forces to insert a bone penetrating needle attached to a cartridge assembly at a selected target site. A plunger operating and cartridge drive mechanism incorporating teachings of the present disclosure may also apply longitudinal or axial force to a cartridge assembly to insert an attached bone penetrating needle into bone marrow at a selected target site. Examples of drivers which apply linear force (sometimes referred to as "impact drivers" or "impact driver devices") are shown in U.S. patent application Ser. No. 11/064,156 entitled "Impact-Driven Intraosseous Needle" filed Feb. 23, 2005. Such drivers may be satisfactorily used with a cartridge assembly incorporating teachings of the present disclosure.

Drive housing 54 may be described as having a hollow, generally cylindrical configuration defined in part by longitudinal bore 56. Plunger operating assembly 82 may be slidably disposed within longitudinal bore 56 which extends between first end 54a and second end 54b of rotational housing 54. Portions of plunger operating assembly 82 may extend from first end 54a of rotational housing 54. See FIGS. 1B, 1C, 1D and 1H. First end 54a of rotational housing 54 may also be operable to releasably engage a cartridge assembly incorporating teachings of the present disclosure with plunger and drive mechanism 50.

Second end 54b of drive housing 54 may be securely engaged with drive shaft 38. For embodiments such as shown in FIGS. 1B, 1C and 1D, coupling 42 may be securely engaged with exterior portions of drive shaft 38 and interior portions of rotational housing 54 proximate second end 54b. Various types of mechanical fasteners such as set screws, pins, and/or detents may be satisfactorily used to engage coupling 42 with drive shaft 38 and drive housing 54. Engagement between second end 54b and drive shaft 38 generally prevents longitudinal movement of drive housing 54 relative to receiver portion 26 of housing 22.

The exterior dimensions and configurations of drive housing 54 may be selected to allow rotation of drive housing 54 with respect to retractable sleeve 58 and other components associated with plunger operating and cartridge drive mechanism 50. Drive housing 54 may also be rotatably disposed within various components associated with housing 22 such as receiver portion 26 and interior support 23b.

Plunger operating assembly 82 may be triggered or activated to apply force to a plunger assembly associated with a cartridge assembly engaged with first end 54a of drive housing 54 to inject fluids from the cartridge assembly into bone marrow at a target site. Plunger operating assembly 82 may have a first, retracted or cocked position such as shown in FIGS. 1B and 1G and a second, extended or released position such as shown in FIGS. 1D and 1H. Plunger operating assembly 82 preferably includes first end 82a which may extend from first end 54a of drive housing 54. Second end 82b of plunger operating assembly 82 may be disposed adjacent to coupling 42 when plunger operating assembly 82 is in its first retracted or cocked position. See FIG. 1B. As discussed later in more detail, pawl latch assembly 110 may be releasably engaged with shoulder 88 to hold plunger operating assembly 82 in its first, retracted or cocked position. See FIGS. 1B and 1G.

Plunger operating assembly 82 may sometimes be described as a "plunger barrel." Plunger operating assembly 82 may have a generally cylindrical configuration defined in part by reduced outside diameter portion 84 and enlarged outside diameter portion 86. See FIGS. 1G and 1H. Shoulder 88 may be formed on the exterior of plunger operating assembly 82 between reduced outside diameter portion 84 and enlarged inside diameter portion 86. Reduced outside diameter portion 84 may include a generally hollow, cyndrical chamber or cavity 94.

A plunger rod or plunger shaft extending from an associated cartridge assembly may be disposed within cavity 94. For example, FIGS. 1C and 1D show cartridge assembly 130 releasably engaged with first end 54a of drive housing 54 and portions of plunger shaft 142 extending from cartridge assembly 130 into cavity 94. During loading of apparatus 20, portions of plunger shaft 142 extending from cartridge assembly 130 or plunger shaft 142a extending from cartridge assembly 130a may be inserted into cavity 94.

Enlarged outside diameter portion 86 (FIG. 1B) may include generally hollow, cylindrical chamber or cavity 96 with portions of first spring or plunger spring 51 disposed therein. When plunger operating assembly 82 is released from its first position by activation of pawl latch assembly 110, first spring 51 may provide sufficient force or energy to propel plunger shaft 142 and attach plunger or piston 144 into attached cartridge assembly 130 to inject fluids from cartridge assembly 130 into bone marrow at a target site.

Plunger and drive mechanism 50 may also include retractable sleeve 58 slidably disposed within housing 22. Sleeve 58 may be described as a generally elongated, hollow cylinder defined in part by first end or distal end 58a and second end or proximal 58b. Sleeve 58 may have a first, extended position such as shown in FIGS. 1A, 1B and 1C and a second, retracted position such as FIG. 1D.

As shown in FIGS. 1A-1D, cut-out or window 60 may be formed in sleeve 58 proximate first end or distal end 58a. Window 60 may be used to confirm that a cartridge assembly has been loaded and properly seated into apparatus 20. For some applications a retractable sleeve may be formed from clear, plastic-type material (not expressly shown) which would not require the use of cut-out or notch 60 to indicate when a cartridge assembly has been releasably installed within apparatus 20.

Figure 1E:
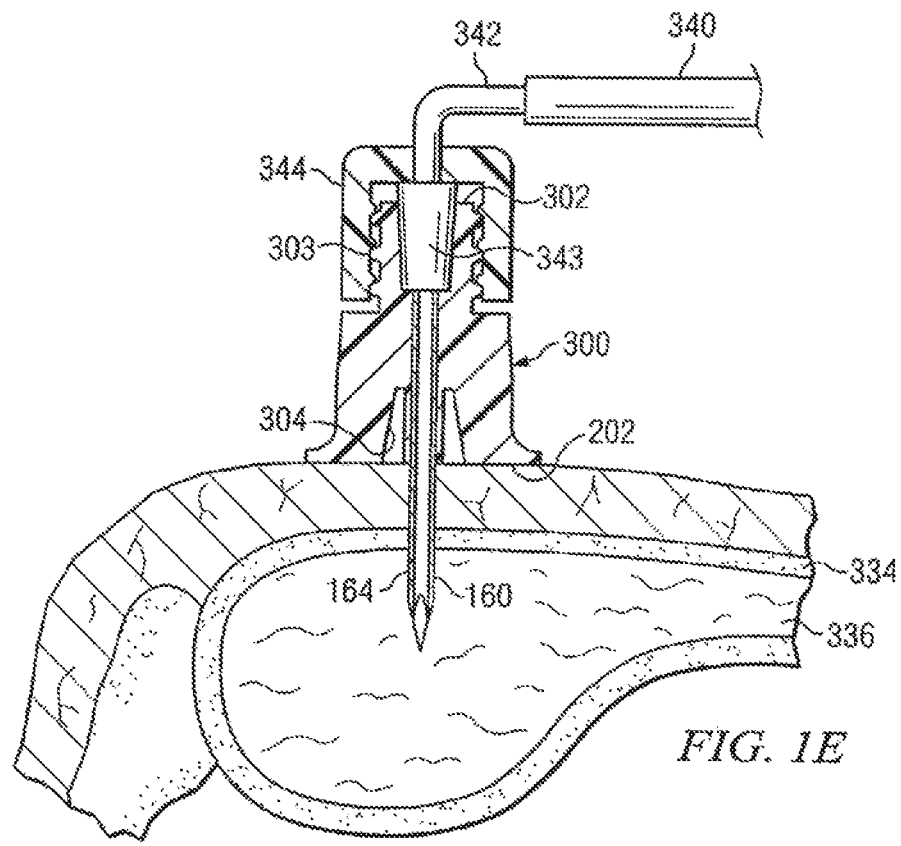
FIG. 1E is a schematic drawing in section and in elevation with portions broken away showing a bone penetrator communicating with bone marrow in accordance with teachings of the present disclosure.
Figure 1F:
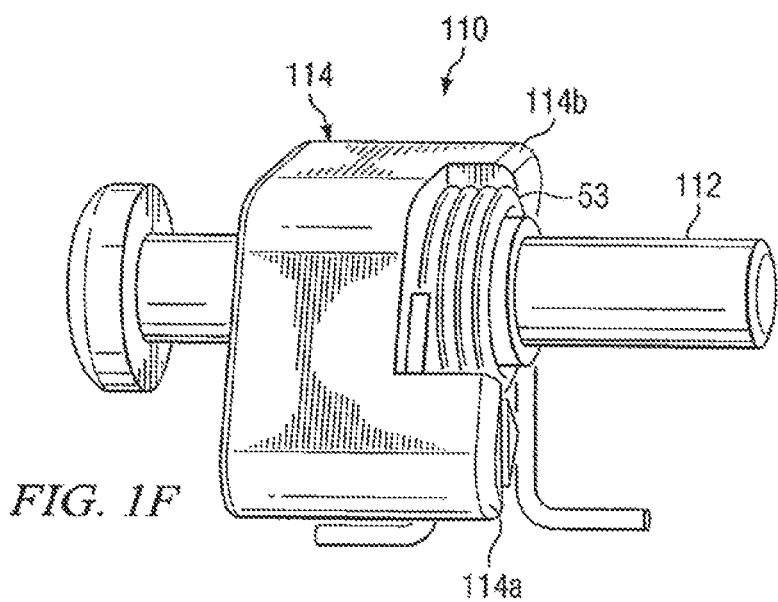
FIG. 1F is a schematic drawing showing an isometric view with portions broken away of one example of a pawl latch assembly satisfactory for use with the apparatus of FIGS. 1B-1D.
Figure 1G:
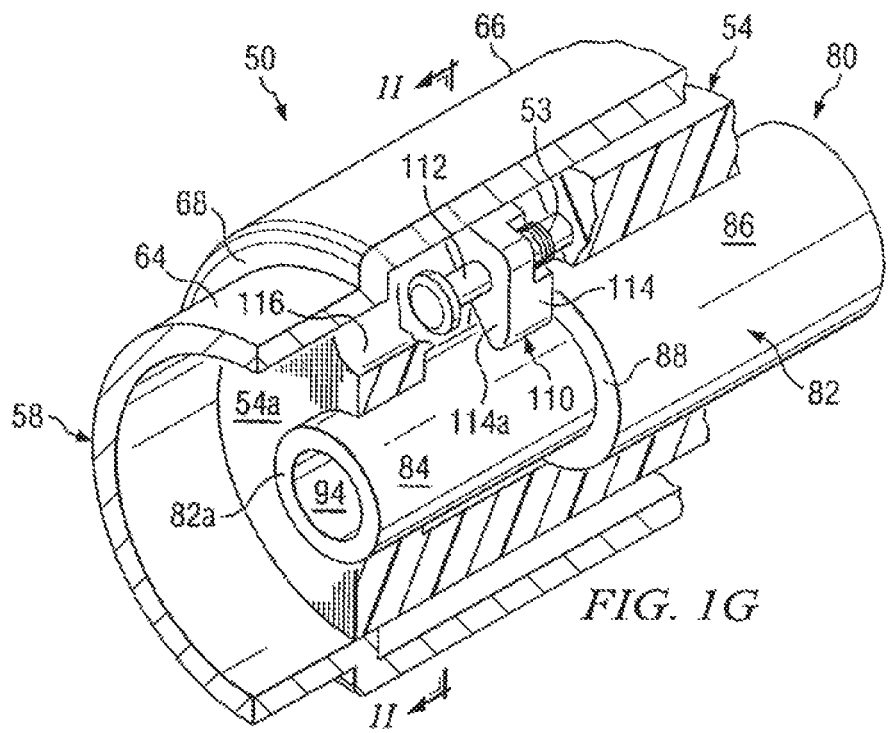
FIG. 1G is a schematic drawing showing an isometric view with portions broken away of a pawl latch assembly holding a plunger operating assembly or plunger barrel in a first, cocked position.
Figure 1H:
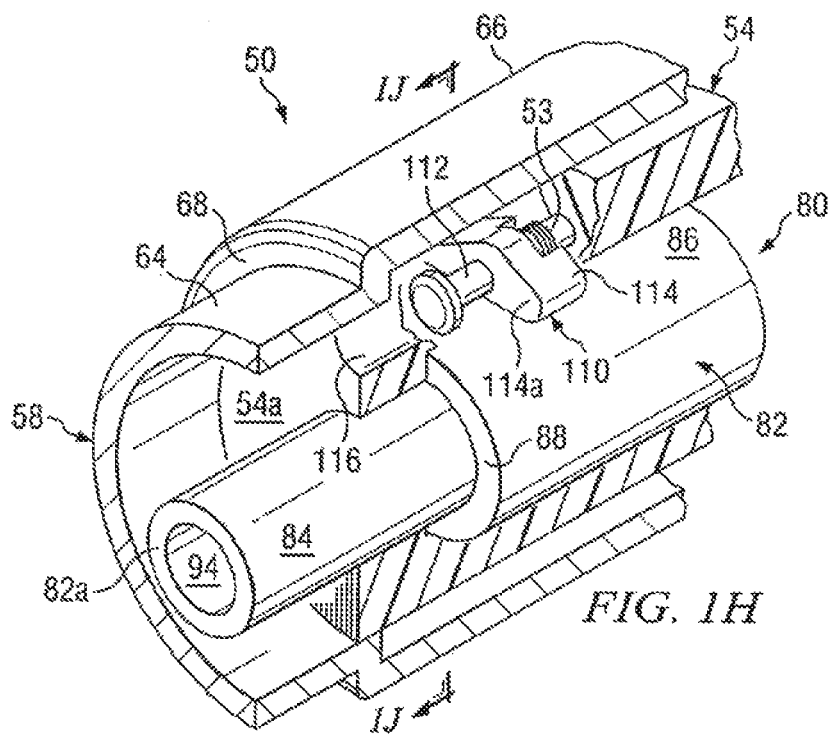
FIG. 1H is a schematic drawing showing an isometric view in section with portions broken away of the pawl latch assembly and plunger operating assembly of FIG. 1G in a second, released position.
Figure 1I:
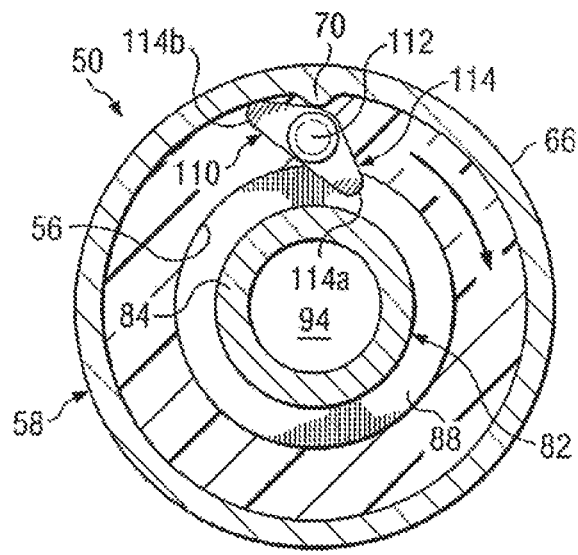
FIG. 1I is a schematic drawing in section taken along lines 1I-1I of FIG. 1G.
Figure 1J:
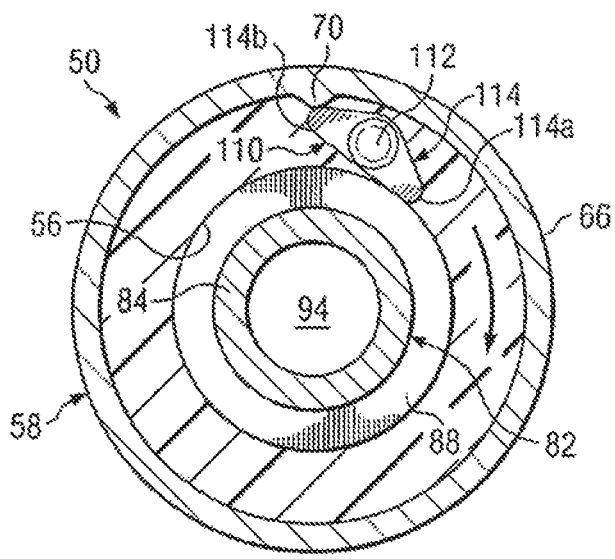
FIG. 1J is a schematic drawing in section taken along lines 1J-1J of FIG. 1H.

As shown in FIGS. 1B-1D and 1G-1J, sleeve 58 may include reduced outside diameter portion 64 and enlarged outside diameter portion 66 with shoulder 68 formed there between. Ramp or trigger 70 may be formed on the inside diameter of sleeve 58 proximate shoulder 68. See FIGS. 1C, 1I and 1I. Ramp 70 may contact pawl latch assembly 110 while drive housing 54 is rotating to release plunger operating assembly 82 when an associated cartridge assembly has been inserted to a desired depth at a target site. As shown in FIGS. 1D, 1I and 1J, longitudinal movement or sliding of sleeve 58 from first end 27 of housing 22 towards second end 28 of housing 22 will result in ramp 70 contacting portions of pawl latch assembly 110 when drive housing 54 is rotating. Movement of retractable sleeve 58 from its first extended position to a second retracted position will generally not result in ramp 70 contacting or releasing pawl latch assembly 110.

For some applications, receiver portion 26 of housing 22 may include first interior support 23a and second interior support 23b. See FIGS. 1B, 1C and 1D. Interior supports 23a and 23b are preferably spaced from each other and securely engaged with receiver portion 26. For some applications interior supports 23a and 23b may have a generally circular opening formed therein (not expressly shown). The opening in first interior support 23a may be sized to slidably receive reduced outside diameter portion 64 of sleeve 58. As shown in FIGS. 1B and 1C interior support 23a may engage or contact shoulder 66 when sleeve 58 is in its first, extended position.

Second interior support 23b may have a generally circular opening formed therein (not expressly shown) and may be sized to be compatible with the outside diameter of drive housing 54. See FIGS. 1B-1D. Second spring 52 maybe disposed within receiver portion 26 of housing 22 between second support 23b and a recess defined in part by shoulder 72 formed on the interior of enlarged outside diameter portion 66 of sleeve 58. Portions of drive housing 54 may be disposed within second spring 52. See FIG. 1C.

When a bone penetrating needle of an associated cartridge assembly is inserted into bone marrow at a target site, sleeve 58 will generally retract or slide from first end 27 of housing 22 towards second end 28 of housing 27. See FIG. 1D. This movement will compress second spring 52 between second support 23b and shoulder 72 formed on the interior of enlarged outside diameter portion 66. When apparatus 20 is removed from contact with a patient's skin, second spring 52 will return sleeve 58 to its first, extended position as shown in FIG. 1B with shoulder 68 contacting first support 23a.

Movement of retractable sleeve 58 from its first, extended position (FIGS. 1B and 1C) to its second, retracted position (FIG. 1D), as an associated bone penetrating needle is inserted into bone marrow at a target site, may result in pawl latch assembly 110 contacting ramp or trigger 70 during rotation of drive housing 54. See FIGS. 1I and 1J. Ramp 70 will then move pawl latch assembly 110 from its first, blocking position (FIGS. 1B and 1G) to its second position (FIGS. 1D and 1J) which results in release of plunger operating assembly 82 from its first, cocked position such as shown in FIG. 1B. First spring 51 may then move plunger operating assembly 82 to its second, released or fired position such as shown in FIG. 1D. Pawl latch assembly 110 is only one example of a mechanism satisfactory for releasing a plunger operating assembly from a cocked position.

FIG. 1E shows bone penetrator 160 inserted into bone 334 and associated bone marrow 336. Bone 334 may be generally described as a humeral head. For some applications a humeral head may be a preferred target site due to relatively high blood flow rates through associated bone marrow and relatively easy access. Various types of connections may be used to communicate fluids with bone marrow 336 via bone penetrator 160 and intravenous tubing 340. For example right angle connector 342 may be engaged with one end of tubing 340. Right angle connector 342 has the advantage of allowing tubing 340 to be connected to bone penetrator 160 at an angle that will not kink or pinch off the lumen of tubing 340. Right angle connector 342 may also include Luer fitting 343 sized to be inserted into end 302 of hub 300. Locknut 344 may be used to engage right angle connector 342 with threaded connection 303 adjacent to second end 302 of hub 300.

Many medical devices such as syringes, hypodermic needles, catheters, IV tubing and stop cocks may include either a pin (male) or box (female) Luer type fitting. The pin end or box end may include threads which allow releasably engaging an associated medical device with other equipment having a complimentary Luer type fitting. Luer type connections may sometimes be described as Luer slips or Luer locks. Luer slips may require a half twist of an associated collar to securely engage a pin end and a box end with each other. A Luer lock functions by forming a watertight fit between a pin and a box when engaged and when twisted by a half turn or more. Luer looks frequently include a threaded looking collar on a box end which mates with ears or projections from an associated pin end to provide a more positive, locked connection. Luer connections generally form fluid tight seals. Some Luer connections may include tapered fittings.

For some applications second end 302 of hub 300 may be modified to have one or more features of such previously described Luer connections. Second end 302 and threaded connection 303 of hub 300 may be designed to accommodate attachment of various types of connectors used to communicate fluids with bone marrow or other target sites via bone penetrator 160.

FIG. 1E illustrates only one example of a connector that may be used to communicate fluids between bone penetrator 160 and tubing 340. Intravenous tubing may be used to provide intravenous fluids and/or medications to associated bone marrow. The tubing may also be used in withdrawing a sample of blood from the bone marrow. Other connectors or adapters may also be used to connect a penetrator to intravenous tubing, other types of tubing and/or a syringe.

As shown in FIGS. 1B, 1C, 1D and 1F-1J pawl latch assembly 110 may be disposed within portions of drive housing 54 intermediate first end 54a and second end 54b. Pawl latch assembly 110 may include pivot shaft 112 with pawl or cam 114 rotatably mounted thereon. Pawl 114 may include first lobe 114a and second lobe 114b extending from pivot shaft 112. First lobe or first portion 114a may be sized to releasably engage shoulder 88 formed on the exterior of plunger operating assembly 82. Second lobe or second portion 114b may be sized to engage ramp or trigger 70. Third spring or pawl spring 53 may also be mounted on pivot shaft 112 and engaged with pawl 114.

Pawl 114 may have a first position such as shown in FIGS. 1B and 1G which corresponds with the first, cocked position of associated plunger operating assembly 82. Third spring 53 preferably biases pawl 114 to its first position which releasably engages first lobe 114a with shoulder 88. Pawl 114 may have a second position which corresponds with the second, released position for plunger operating assembly 82. See FIGS. 1D and 1H.

For some applications drive housing 54 may include opening or channel 116 extending from first end 54a. Opening or channel 116 may be sized to accommodate insertion of pivot pin 112 into associated pawl 114 and third spring 53. See FIGS. 1G and 1H. Drive housing 54 may also include opening or channel 118 sized to receive the opposite end of pivot shaft 112. See FIGS. 1B and 1D. A window or notch maybe formed in the exterior of drive housing 54 to allow inserting portions of pawl 114 including lobe 114b therethrough.

When plunger operating assembly 82 is in its first, cocked position, second lobe or second portion 114b of pawl 114 will be spaced longitudinally from ramp or trigger 70. During rotation of an associated cartridge assembly and insertion of a bone penetrator at a target site, retractable sleeve 58 will slide longitudinally relative to the exterior of drive housing 54. The longitudinal movement of retractable sleeve 58 in combination with rotation of drive housing 54 will result in ramp or trigger 70 engaging second lobe 114b which rotates pawl 114 on pivot pin 112. Such rotation results in first lobe 114a releasing or allowing plunger operating assembly 82 to move from its first, cocked position to its second, released position. As previously discussed, this movement may result in injection of fluids from cartridge assembly 130 through penetrator 160 into bone marrow at a target site.

Cartridge assemblies formed in accordance with teachings of the present disclosure may include a fluid reservoir having a generally hollow, cylindrical configuration defined in part by a first, distal end and a second, proximal end. A hub with a hollow, bone penetrating needle may be attached to the first, distal end. Portions of a plunger assembly may be slidably disposed within the fluid reservoir to force fluids contained in the fluid reservoir through an attached hollow, bone penetrating needle. The plunger assembly may include a plunger shaft and plunger piston. Portions of the plunger shaft may extend from the second, proximal end of the fluid reservoir.

For some applications, cartridge assemblies incorporating teachings of the present disclosure may be prefilled with a specific fluid using techniques associated with prefilled syringes. For other applications, cartridge assemblies incorporating teachings of the present disclosure may normally be empty until filled with a fluid or medication prior to use of each cartridge assembly. Cartridge assemblies incorporating teachings of the present disclosure will often be disposed of after a single use. However, for some applications, cartridge assemblies incorporating teachings of the present disclosure may be used multiple times and may be used at one or more target sites.

Cartridge assemblies and associated fluid reservoirs may have a wide variety of configurations and functions similar to a hypodermic syringe, an insulin syringe or a tuberculin syringe. For example, fluid reservoirs 132 and 132a (FIGS. 2A and 2C) may contain a quantity of fluid with medication or a drug for delivery to bone marrow or another selected target site. The medication or drug may often be available in liquid form. However, any suitable form of drug including solid, powder, capsule or any other known form may be used. Medication or drugs may include, for example, emergency drugs for cardiac resuscitation, antibiotics, antidotes and any other drug suitable for administration to a body. Fluid reservoirs 132 and 132a may also be used for injection of intravenous fluids or any other substance desired for a specific purpose.

Various features of the present disclosure may be described with respect to cartridge assemblies 130 and 130a as shown in FIGS. 2A-2D. Cartridge assemblies incorporating teachings of the present disclosure may have some characteristics associated with medical syringes. However, various components associated with cartridge assemblies 130 and 130a may be modified in accordance with teachings of the present disclosure to accommodate insertion of an associated hollow, bone penetrating needle into bone marrow or other selected target sites.

Cartridge assembly 130 may include barrel or fluid reservoir 132 having a generally hollow, cylindrical configuration defined in part by inside diameter 134. Barrel 132 may include first end 131 and second end 133. Hub 300 and associated hollow bone penetrating needle or bone penetrator 160 may be releasably engaged with first end 131. Barrel 132 may be formed from reusable glass, disposable plastic, glass composite, plastic composites and any other material suitable to contain fluids depending upon intended uses for cartridge assembly 130. Barrel 132 may sometimes be described as an "ampoule."

Various types of plunger assemblies may be satisfactorily used with a cartridge assembly incorporating teachings of the present disclosure. For some applications plunger assembly 140 may include plunger shaft or plunger rod 142 and plunger piston 144. For some applications first end 145 of plunger shaft 142 may be releasably engaged with plunger piston 144. For other applications plunger shaft 142 may be securely engaged with plunger piston 144. One or more projections 146 may be formed on the outside diameter of plunger piston 144 to form a generally fluid tight, moveable seal with respect to inside diameter 134 of barrel 132. Plunger piston 144 may also function as a fluid seal or stopper to maintain any fluids contained within fluid reservoir 132 prior to loading cartridge assembly 130 into apparatus 20 or 220. Various types of elastomeric materials may be satisfactorily used to form plunger piston 144.

Plunger assembly 140 may slidably move from second end 133 of barrel 132 toward first end 131 in response to an axial force applied to plunger shaft 142. Release of plunger operating assembly 82 from its first, retracted or cocked position (FIG. 1B) allows first spring or plunger spring 51 to apply an axial force or a longitudinal force to plunger shaft 142 and move piston 144 from its first position adjacent to second end 133 to a second position adjacent to first end 131 of fluid reservoir 132 (FIG. 1D). Such movement of piston 144 may result in fluid from barrel 132 being injected through bone penetrating needle 160 into bone marrow or another target site.

Piston 144 may include recess 148 sized to receive threaded connection 303 formed adjacent to second end 302 of hub 300. Engagement of piston 144 with the threaded connection 303 may allow disengagement of reservoir 132 from hub 300. Drive connector 150 may be securely engaged with second end 133 of barrel 132 opposite from hub 300 (FIGS. 2A and 2B).

Drive connector 150 may have one or more recesses 152 formed therein and sized to receive corresponding segment 154 extending from first end 54a of drive housing 54. See for example FIGS. 4A and 4B. The dimensions of each recess 152 may be selected to form a secure, snug fit with associated segment 154. Rotation of drive housing 54 will result in each segment 154 contacting associated recess 152 to rotate drive connector 150 and attached barrel 132. The connection formed between hub 300 and first end 131 of barrel 132 is preferably designed to allow transfer of such rotation to attached bone penetrating needle 160.

Figure 2A:
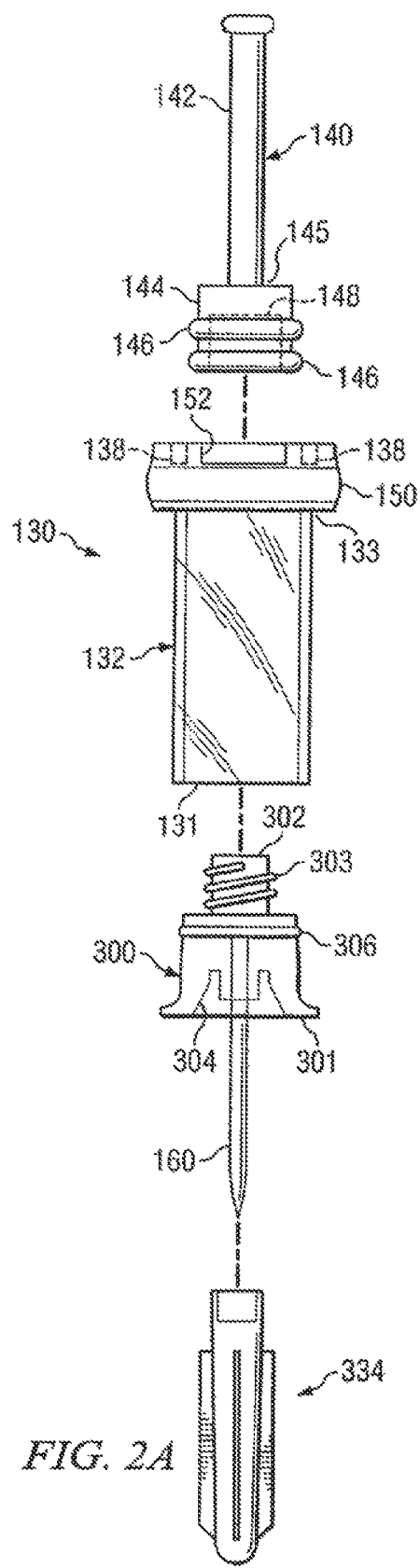
FIG. 2A is a schematic, exploded drawing in elevation showing one example of a cartridge assembly satisfactory for use with an apparatus operable to deliver a quantity of medication to bone marrow.
Figure 2B:
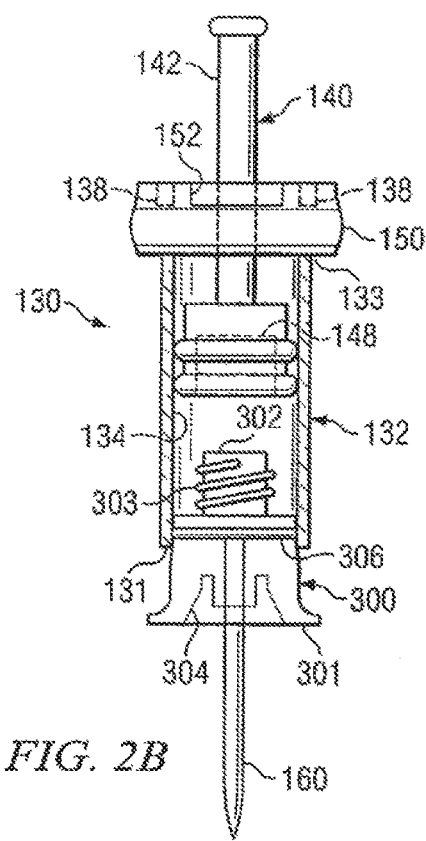
FIG. 2B is a schematic drawing in elevation and in section showing the cartridge assembly of FIG. 2A.

As shown in FIGS. 2A and 2B, a plurality of magnets 138 may be disposed in drive connector 150 at locations which allow forming a releasable magnetic engagement with first end 54a of drive housing 54. Recesses 152, segments 154 and magnets 138 cooperate with each other to allow releasable engagement between cartridge assembly 130 and first end 54a of drive housing 54.

As shown in FIGS. 1E, 2A and 2B, hub 300 may be used to stabilize an attached bone penetrator such as, but not limited to, bone penetrating needle 160 during insertion into a patient's skin, soft tissue and adjacent bone or other target site. The combination of hub 300 with bone penetrator 160 may sometimes be referred to as a penetrator set or intraosseous needle. First end 301 of hub 300 may have a size and configuration compatible with a selected target site for inserting bone penetrator 160. Examples of such target sites include, but are not limited to, a humeral head, a tibia, or a sternum. Second end 302 and threaded connection 303 of hub 300 may be operable to be releasably engaged with barrel 132. End 131 of barrel 132 may have a generally circular opening sized to receive second end 302 of hub 300 therein. Optional O-ring 306 or any other suitable fluid seal may be disposed on exterior portions of hub 300 to form a fluid barrier between adjacent interior portions of barrel 132. See FIGS. 2A and 2B.

Cartridge assembly 130a as shown in FIGS. 2C and 2D may include barrel or fluid reservoir 132a having a hollow, generally cylindrical configuration defined in part by inside diameter portions 134a, 134b and 134c. Barrel 132a may include first end 131a and second end 133. Hub 300 and associated bone penetrating needle 160 may be engaged with first end 131a. Barrel 132a may be formed from materials such as used to form barrel 132.

Various types of plunger assemblies may be satisfactorily used with cartridge assembly 130a. For some applications plunger assembly 140a may include plunger shaft or plunger rod 142a and plunger piston 144a. For some applications, first end 145 of plunger shaft 142a may be securely engaged with plunger piston 144a. For other applications, first end 145 may be releasably engaged with piston 144a such as shown in FIGS. 2D, 4B, 7B and 8B.

One or more projections 146 may be formed on the outside diameter of plunger piston 144a to form a generally fluid tight, moveable seal with respect to inside diameter portion 134a. First end 147 of piston 144a may be configured to form a generally fluid tight seal with tapered interior surface 134b of barrel 132a. Plunger piston 144a may also function as a fluid seal or stopper to maintain fluids contained within reservoir 132a prior to inserting cartridge assembly 130a into apparatus 200 or 220. Various types of elastomeric materials may be satisfactorily used to form plunger piston 144a.

Plunger assembly 140a may slidably move from second end 133 of barrel 132a towards first end 131a in response to an axial force applied to plunger shaft 142a. Release of plunger operating assembly 82 from its first, retracted position allows first spring or plunger spring 51 to apply an axial force or a longitudinal force to move piston 144a from its first position adjacent to second end 133 to a second position which forms a generally fluid tight seal with tapered, inside diameter portion 134b of barrel 132a.

As shown in FIGS. 2C and 2D, second end 302 of hub 300a may also be engaged with barrel 132a. End 131a of barrel 132a may include reduced inside diameter portion 134 c with threads 137 formed therein. The dimensions of inside diameter portion 134c may be selected to be compatible with the outside diameter of second end 302 of hub 300a. Second end 302 of hub 300a may include threads 303 or other suitable fitting formed on the exterior therein. Threads 303 may be engaged with threads 137. Second end 302 may have a generally cylindrical pin type configuration compatible with engaging first end or box end 131a of barrel 132a. For many applications hub 300a will remain securely engaged with first end 131a of barrel 132a during use of associated cartridge assembly 130a.

For some applications first end 301 of hub 300a may have the general configuration of a flange. Slot or groove 304 may be formed in first end 301 and sized to receive one end of protective cover or needle cap 334. Slot or groove 304 may be used to releasably engage cover 334 with hub 300a.

As shown in FIGS. 2C and 2D, a plurality of ridges 320 may be formed on exterior portions of hub 300a to allow an operator to grasp the associated penetrator assembly or penetrator set while loading an associated cartridge assembly into apparatus 20 or 220. Ridges 320 may also aid in removal of bone penetrator 160 from a target site. Longitudinal ridges 320 may also be grasped for engagement and/or disengagement of hub 300a with first end 131a of barrel 132a.

The dimensions and configuration of first end 301 of hub 300a may be varied to accommodate various target sites and/or patients. Hub 300a may be satisfactorily used with a wide variety of flanges or other configurations compatible with contacting a patient's skin. The present disclosure is not limited to hub 300a or bone penetrator 160.

For some applications a cartridge assembly may include only a single hollow bone penetrating needle. For other applications a cartridge assembly may include an outer penetrator such as a cannula or hollow bone needle or hollow drill bit (not expressly shown) and an inner penetrator such as a stylet, trocar or other removable device (not expressly shown) disposed within the outer penetrator. For some embodiments bone penetrating needles 160 and 160a may include a stylet (not expressly shown).

Penetrators may be relatively small for pediatric patients, medium-sized for adults and large for oversized adults. The length and diameter of the penetrator used in a particular application may depend upon the size of a bone to which the apparatus may be applied. Penetrators may be provided in a wide variety of configurations depending upon intended clinical purposes for insertion of the associated penetrator assembly. For example, there may be one configuration for administering drugs or fluids to a patient's bone marrow and an alternative configuration for sampling bone and/or blood from a patient. Other configurations may be appropriate for bone and/or tissue biopsy. Some penetrators may be suitable for more than one purpose. The configuration and size of a bone penetrator may also vary depending upon the target site chosen for insertion of each penetrator. The present disclosure is not limited to bone penetrators 160 or 160a.

A wide variety of hollow bone penetrating needles and hollow drills may be satisfactorily used to deliver a quantity of medication to bone marrow or other target sites in accordance with teachings of the present disclosure. Hollow, bone penetrating needles 160 and 160a as shown respectively in FIGS. 3A and 3B are representative of only two examples of bone penetrators that may be satisfactorily used with apparatus of the present disclosure. Bone penetrators 160 and 160a are examples of a single, hollow penetrator. The size of bone penetrators 160 and 160a may vary depending upon a selected target site and/or intended applications for an associated cartridge assembly.

Bone penetrating needles 160 and 160a may be formed of stainless steel or any other suitable material. Respective closed tips 162 suitable for drilling through a bone into associated bone marrow, may be formed on a respective first end of bone penetrators 160 and 160a. Closed tip 162 may include at least one cutting edge 170 that enables efficient drilling through bone to associated bone marrow with minimal trauma to respective outer bony cortex.

Outside diameter or exterior portion 168 of bone penetrators 160 and 160a may be selected to accommodate secure engagement with an associated hub. A second end of each bone penetrator 160 and 160a opposite from respective tip 170 may be sized to receive fluid from an attached cartridge assembly.

Bone penetrators 160 and 160a may include one or more side ports 164 for release of medication or communication of fluid with adjacent bone marrow. Side ports 164, holes in the side of bone penetrators 160 and 160a, may be configured to block passage of bone chips and debris into longitudinal bore 166. By way of example and not limitation, one way to configure side ports 164 is to angle each side port 164 in a direction that is opposite to the direction of drilling. Alternatively, bone penetrating needle 160 and 160a may include a sleeve expressly shown) that blocks passage of bony fragments into longitudinal bore 166 of bone penetrator 160 or 160a.

FIG. 3C is a schematic drawing in section showing side port 164 offset or angled relative to longitudinal axis 169 of longitudinal bore 166. One or more side ports 164 may be formed at an acute angle relative to associated longitudinal bore 166 and longitudinal axis 169 to minimize obstruction or clogging of each side port 164 and associated longitudinal bore 166 by bone fragments (not expressly shown) and/or soft body tissue (not expressly shown). For example if drilling occurs in a clockwise direction, side ports 164 may be angled counter clockwise. See FIG. 3C.

Figure 4A:
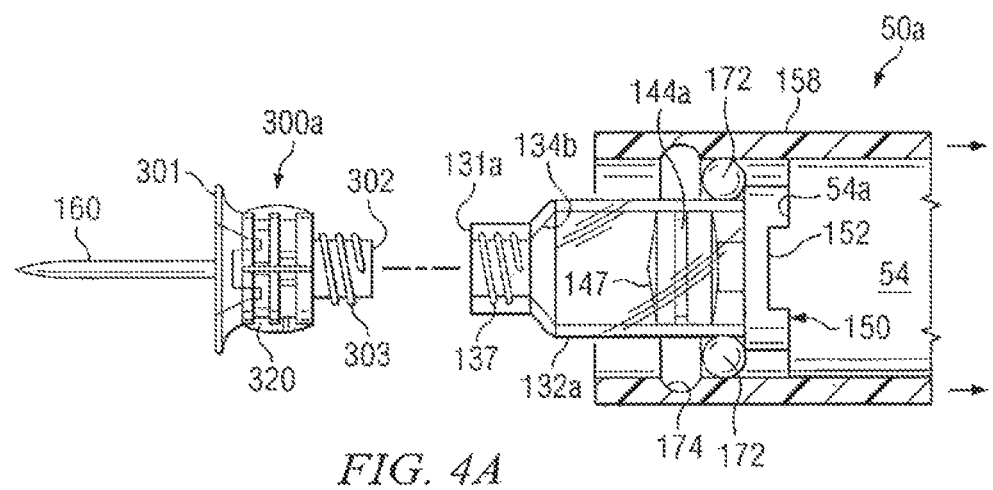
FIG. 4A is an exploded, schematic drawing in section and in elevation with portions broken away showing one example of a cartridge assembly releasably engaged with a plunger operating and cartridge drive mechanism incorporating teachings of the present disclosure.
Figure 4B:
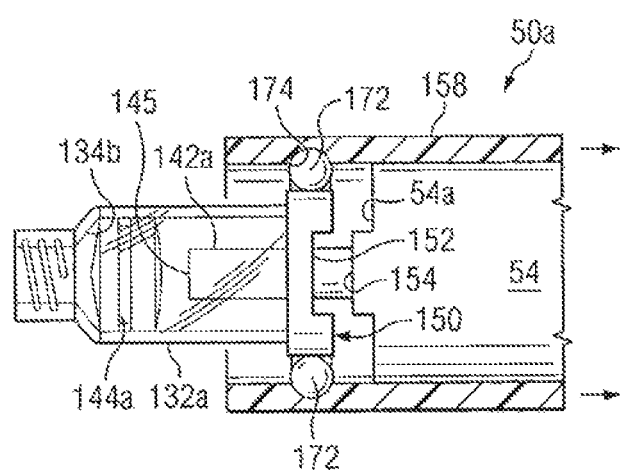
FIG. 4B is a schematic drawing in section and in elevation with portions broken away showing release of the cartridge assembly of FIG. 4A from the plunger operating and cartridge drive mechanism in accordance with teachings of the present disclosure.

FIGS. 4A and 4B show another mechanism satisfactory for releasably engaging a cartridge assembly with portions of a plunger operating and cartridge drive mechanism in accordance with teachings of the present disclosure. However, a wide variety of releasable mechanisms other than magnets 138 such as shown in FIGS. 2A-2D or ball detent mechanisms such as shown in FIGS. 4A and 4B or collet latch mechanisms such as shown in FIGS. 7A, 7B, 8A and 8B may be satisfactorily used with an apparatus operable to deliver fluid to bone marrow in accordance with teachings of the present disclosure.

One of the features of such ball detent mechanisms and collet latch mechanisms includes maintaining positive engagement between an associated plunger operating and cartridge drive mechanism and an attached cartridge assembly until after an associated plunger assembly has moved from a first position to a second position. Such movement may result in fluids contained in the cartridge assembly being injected at a target site before disengagement of the cartridge assembly from the plunger operating and cartridge drive mechanism.

Plunger operating and cartridge drive mechanism 50a such as shown in FIGS. 4A and 4B may include retractable sleeve 158 which functions similar to previously described retractable sleeve 58. Retractable sleeve 158 may include groove or recess 170 formed on the inside diameter of retractable sleeve 158. Balls 172 cooperate with drive connector 150 to maintain positive engagement between cartridge assembly 132a and first end 54a of drive housing 54 until after fluid has been injected from cartridge assembly 132a.

As an associated drive apparatus inserts bone penetrator 160 to a desired depth at a target site, retractable sleeve 158 will move to its second position which allows balls 172 to move radially outward into recess 170. See FIG. 4B. Movement of balls 172 into recess 170 may allow disengagement of drive connector 150 from first end 54a of drive housing 54. Portions of plunger shaft 142a may slide out of cavity 94 in plunger operating assembly 82. See FIG. 4B. After plunger operating and cartridge drive mechanism 50a has inserted bone penetrator 160 at a target site and plunger shaft 142a has moved piston 144 from its first position to its second position proximate inside diameter portion 134a, the associated drive apparatus may be disengaged from cartridge assembly 132a. End 145 of plunger shaft 142a may also be disengaged from piston 144a.

Figure 5:
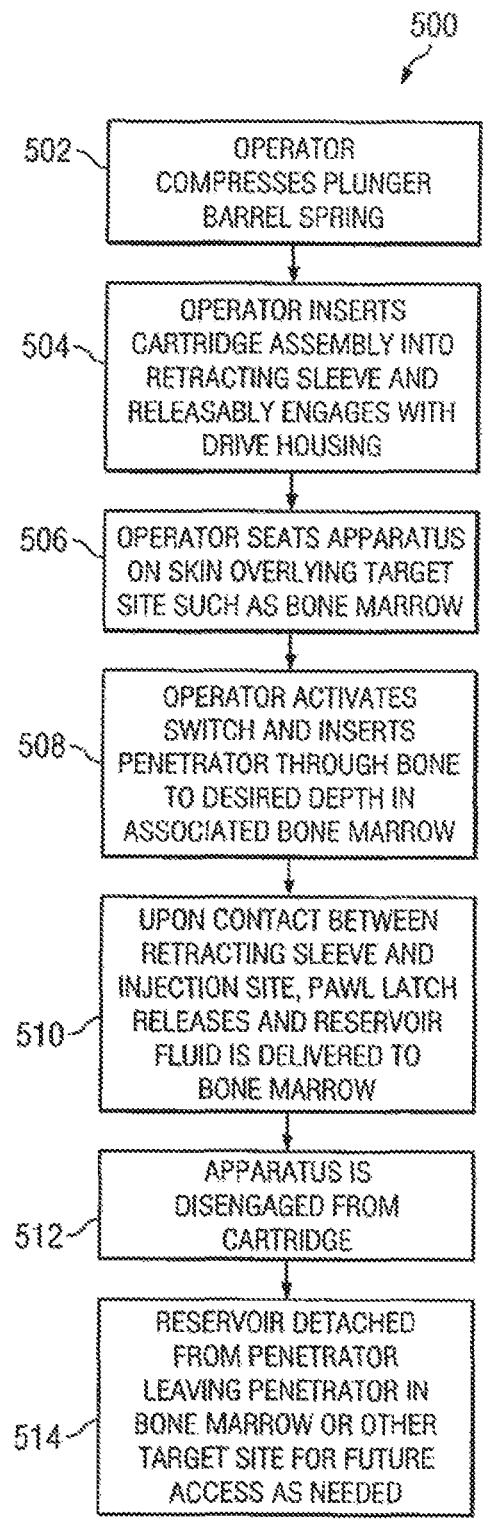
FIG. 5 is a block diagram showing one method of delivering a quantity of medication to bone marrow.

In one embodiment steps such as outlined in FIG. 5 may be followed to employ apparatus 20 in delivering medication or fluid to bone marrow at a target site. Method 500 may begin with first step 502 which includes manually compressing plunger barrel 82 and plunger barrel spring 52. Plunger barrel 82 may be releasably engaged by pawl latch assembly 110 when plunger barrel spring 52 has been compressed. Step 504 may include inserting or loading cartridge assembly 130 or 130a into retractable sleeve 58 and releasably engaging respective cartridge assembly 130 or 130a with an associated plunger operating and cartridge drive mechanism. In one embodiment, cartridge assembly 130 or 130a may engage drive housing 54 by a magnetic mechanism such as one or more magnetic discs 138.

Once cartridge assembly 130 or 130a is engaged with drive housing 54 and plunger operating assembly 82 is in its compressed position, apparatus 20 may be considered "armed" and ready to "fire" an associated bone penetrator into a target site such as a bone overlying bone marrow. Alternative target sites may include other body tissues or body cavities. Use of apparatus 20 to deliver medication or fluid may be applied to any desirable sites in the body.

After preparing a selected target site, for example a humeral head or a proximal tibia, apparatus 20 may be seated with first end 58a of retractable sleeve 58 disposed against skin overlying a bone and bone marrow at the target site for insertion of bone penetrating needle 160. Switch or trigger 32 may be activated to begin drilling into the bone and adjacent target bone marrow. See FIGS. 1C and 1D. Bone penetrating needle 160 may first penetrate the skin, followed by adjacent soft tissue, outer bone cortex and enter bone marrow at the target site. As first end 58a pushes against tissue overlying a target bone marrow, retractable sleeve 58 will contact pawl latch assembly 110 to release plunger operating assembly 82. As first spring decompresses, plunger operating assembly 82 moves plunger shaft 142 into reservoir 132. As plunger shaft 142 is forced into reservoir 132, fluid or any other substance present within reservoir 132 is forced into the target bone marrow or intraosseous space of a bone.

After medication or fluid delivery, apparatus 20 may be disengaged from cartridge assembly 130. Reservoir 132 may then be detached from hub 300. Bone marrow may then be accessed through a connector attached with second end 302 of hub 300. See FIG. 1E. These steps describe only one embodiment of an apparatus operable to administer fluid such as a drug or medication to a target site. Other mechanisms may or may not include one or more of these steps.

Apparatus 220 as shown in FIG. 6 represents another embodiment operable to provide access to bone marrow or any other target site. Apparatus 220 may have several positions including plunger operating and cartridge drive mechanism 250 in an uncocked and unloaded position (not expressly shown), a cocked and unloaded position (not expressly shown), a cocked and loaded position such as shown in FIG. 6, and a discharge position after fluid has been injected from cartridge assembly 130a at a target site (not expressly shown).

Apparatus 220, as shown in FIG. 6, may include driver 221 with housing 222 and a drive assembly (not expressly shown) disposed therein. The drive assembly may include a motor, gearbox or gear head, and drive shaft 238 extending from housing 222. Driver 221 may sometimes be referred to as "powered" driver. Plunger operating and cartridge drive mechanism 250 may or may not be releasably engaged with driver 221. Plunger operating and cartridge drive mechanism 250 will typically be in an uncocked and unloaded position while engaging drive shaft 238 of driver 221 therewith.

Housing 222 may include handle 224 which has been sized and contoured to fit the hand of an operator (not expressly shown). Handle 224 may include on/off switch or trigger 232. Drive shaft 238 may extend from first end 227 of housing 222. Second end 228 of housing 222 may be sealed or closed to protect various components such as a motor, gearbox or gear head and a power source that may be disposed within housing 222.

Examples of power drivers satisfactory for use with a plunger operating and cartridge drive assembly incorporating teachings of the present disclosure are shown in U.S. Pat. No. 6,183,442 entitled "Tissue Penetrating Device and Methods of Using Same" and U.S. Pat. No. 5,554,154 entitled "Intra-Osseous Needle Drill." Power drivers which may also be satisfactorily used with a plunger assembly incorporating teachings of the present disclosure are shown in U.S. patent application Ser. No. 10/449,530 entitled "Apparatus and Method to Provide Emergency Access to Bone Marrow" filed May 30, 2003 and U.S. patent application Ser. No. 10/449,476 entitled "Apparatus and Method to Access Bone Marrow" filed May 30, 2003. Manual drivers (not expressly shown) may also be satisfactorily used with cartridge drive mechanisms and/or plunger operating assemblies incorporating teachings of the present disclosure to provide access to bone marrow or other target sites in a patient's body.

Plunger operating and cartridge drive mechanism 250 may include first spring 251 and second spring. First spring 251 may sometimes be referred to as "plunger spring" 251. Second spring 252 may sometimes be referred to as "retractable sleeve spring" 252. One or more additional springs may also be disposed within plunger operating and cartridge drive mechanism 250 depending upon mechanisms used to releasably retain a cartridge assembly within plunger operating and cartridge drive mechanism 250 and/or allow plunger operating assembly 280 to move from a first, cocked position to a second, uncocked position.

Plunger operating assembly 280 may be disposed within longitudinal bore 256 of plunger operating and drive mechanism 250 adjacent to second end 254b. Plunger operating assembly 280 may include plunger barrel 282. Plunger barrel 282 may include chamber or cavity 292 which is sized to receive portions of a plunger assembly therein. Plunger operating assembly 280 may be moved from an uncocked position (not expressly shown) to a cocked position such as shown in FIG. 6. A cartridge assembly and bone penetrating needle incorporating teachings of the present disclosure may be inserted into retractable sleeve 258 and releasably engaged with an associated drive connector. Drive connectors 150, 150a, 150b or any other drive connector incorporating teachings of the present disclosure may be used.

First end or distal end 258a of retractable sleeve 258 may then be placed adjacent to a selected target site. Switch 232 may be depressed to activate driver 221 to rotate drive shaft 238 and insert bone penetrating needle 160 to a desired depth at the target site. As bone penetrating needle 160 is inserted into the target site, retractable sleeve 258 will move longitudinally from a first, extended position to a second, retracted position which results in release of plunger operating assembly 280 from its first, cocked position and allows first spring or plunger spring 251 to force plunger assembly 140a to move from its first position to its second position which results in the injection of fluids contained within reservoir 132a into bone marrow at the selected target site. After plunger assembly 140a has completed injection of the fluid, various release mechanisms such as shown in FIGS. 4A, 4B, 7A, 7B, 8A and 8B may be satisfactorily used to disengage cartridge assembly 130a from plunger operating and cartridge drive mechanism 250.

Plunger operating and cartridge drive mechanism 250 may also include drive housing 254 defined in part by first end 254a and second end 254b. Drive housing 254 may have a generally hollow cylindrical configuration defined in part by longitudinal bore 256 extending from first end 254a towards second end 254b. Retractable sleeve 258 may be slidably disposed within longitudinal bore 256 and extend from first end 254a. Retractable sleeve 258 may also include first end or distal end 258a and second end or proximal end 258b. The outside diameter of retractable sleeve 258 and the inside diameter of longitudinal bore 256 are preferably selected to allow longitudinal sliding movement of retractable sleeve 258 from its first, extended position as shown in FIG. 6 to a second, retracted position (not expressly shown).

Second end 254b of drive housing 254 may be generally closed except for opening 262 which is preferably sized to receive drive shaft 23S. Rotation of drive shaft 23S may be transmitted through portions of drive housing 250 adjacent to opening 256. Drive housing 254 may be used to transmit rotational forces or drilling forces from drive shaft 23S to a cartridge assembly releasably engaged with plunger operating and cartridge drive mechanism 250.

FIGS. 7A and 7B show portions of plunger operating and cartridge drive mechanism 50b with cartridge assembly 130a releasably attached thereto. Release mechanism 180 may be generally described as a collet latch assembly having a plurality of collet fingers 182 with respective collet heads 184 disposed on the end of each collet finger 182. Collet latch assembly 180 may be satisfactorily used to releasably engage drive connector 150a of cartridge assembly 130a proximate first end 54a of drive housing 54b.

Plunger barrel 82a may include recess or groove 188 formed on the exterior thereof. As an associated plunger barrel 82a is shifted from a cocked position to a released position, groove 188 will be aligned with second end 186 of collet fingers 182. The dimensions of groove 188 are preferably selected to allow second end 186 of each collet finger 182 to be received therein. An associated retractable sleeve (not expressly shown) may include an enlarged inside diameter portion which accommodates radial expansion of collet fingers 182 and associated collet heads 184 to release their engagement with drive connector 150a. As a result the associated drive apparatus may be removed from cartridge assembly 130a.

Figure 8A:
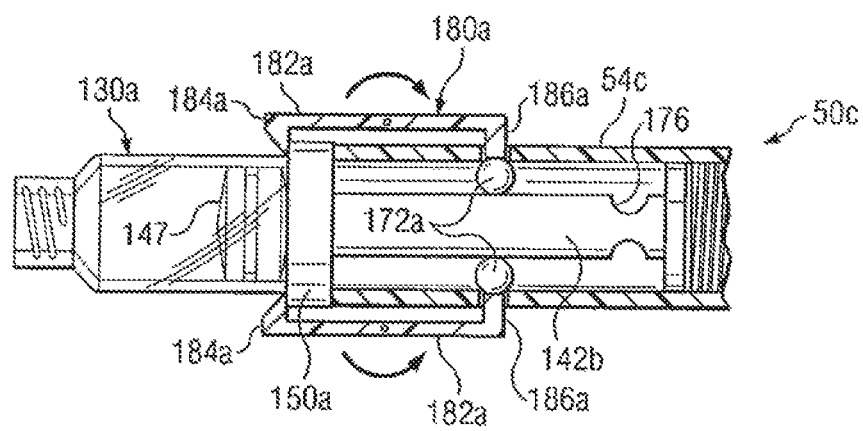
FIG. 8A is a schematic drawing in section and in elevation with portions broken away showing still another example of a cartridge assembly releasably engaged with a plunger operating and cartridge drive mechanism incorporating teachings of the present disclosure.
Figure 8B:
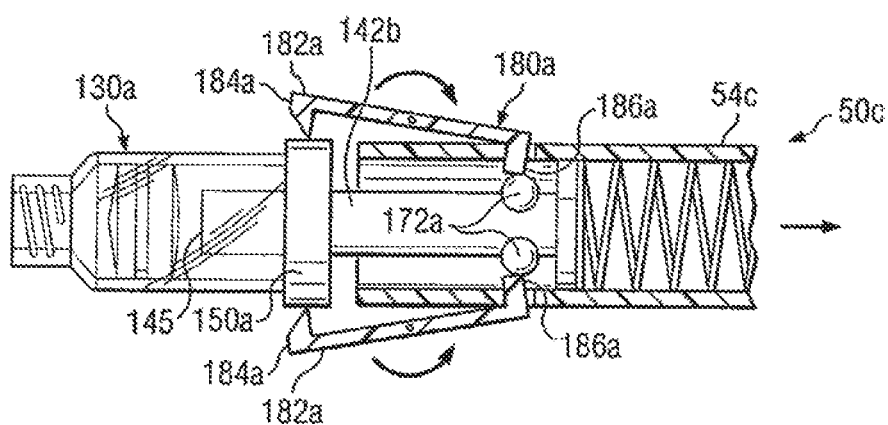
FIG. 8B is a schematic drawing in section and in elevation with portions broken away showing release of the cartridge assembly of FIG. 8A from the plunger operating and cartridge drive mechanism in accordance with teachings of the present disclosure.

FIGS. 8A and 8B show portions of plunger operating and cartridge drive mechanism 50c with cartridge assembly 130a releasably attached thereto. Release mechanism 180a may be generally described as a collet latch assembly having a plurality of collet fingers 182a with respective collet heads 184a disposed on the end of each collet finger 182a. Collet latch assembly 180a may be satisfactorily used to releasably engage drive connector 150a of cartridge assembly 130a proximate first end 54a of drive housing 54c.

Plunger shaft or plunger rod 142b may include recess or groove 176 formed on the exterior thereof. As an associated plunger barrel (not expressly shown) moves from a cocked position to a released position, recess or groove 176 will be aligned with balls 172a and second end 1S6a of each collet finger 182a. The dimensions of recess 176 are preferably selected to allow balls 172a to be received therein. An associated retractable sleeve (not expressly shown) may include an enlarged inside diameter portion which accommodates radial expansion of collet fingers 182a and associated collet heads 184a to release their engagement with drive connector 150a. As a result, the associated drive apparatus may be removed from cartridge assembly 130a.

Apparatus 20 or 220 may be used to access the bone marrow of any bone in the body including but not limited to the tibia, humeral head, or sternum. Apparatus 20 or 220 may be used to access the femur, radius, ulna, iliac crest and medial malleolus or any other target site in a body including non-bony targets. Apparatus 20 or 220 may be used to access the bones and bone marrow of adults, children and any animal species. Apparatus 20 or 200 may also be used to access other tissues or body cavities.

Apparatus 20 and 220 may be used to administer a unit dose of medication to bone marrow or other target sites in any form suitable for delivery. Such drugs include, but are not limited to medications for resuscitation during the treatment of cardiac arrest, antibiotics, poison antidotes, nerve gas antidotes and radio protectants to protect the body against radiation exposure. Apparatus 20 or 220 may be used to administer any suitable fluids or other substances suitable for injection into bone marrow or other sites in the body. Such fluids may include, but are not limited to, normal saline, lactated Ringer's solution, blood, plasma, albumin or any other bio-compatible fluid.

Apparatus 20 and 220 formed in accordance with teachings of the present disclosure may have ergonomic designs that allow insertion pressure or forces, such as rotational, drilling, impact, longitudinal, and/or manual forces, to be applied with relative ease and at the same time permit insertion of a bone penetrator extending from an associated cartridge assembly. Handle 22 and 222 may be aligned with an anatomically neutral position of an operator's hand and wrist as a powered driver rotates a releasably engaged cartridge assembly with a bone penetrator extending therefrom. This alignment may allow better axial orientation of apparatus 20 and 220 as an associated bone penetrator is inserted into bone marrow or other target site with less chance of excessive movement and/or misalignment of the bone penetrator which might result in undesired widening and/or elongation of an associated insertion hole.

Although the present disclosure and its advantages have been described in detail, it should be understood that various changes, substitutions and alternations can be made herein without departing from the spirit and scope of the disclosure as defined by the following claims.

What is claimed is:

1. An apparatus for delivering a quantity of fluid to bone marrow comprising:
    a drive housing comprising a first portion configured to engage a driver assembly and a second portion configured to engage a cartridge assembly, the drive housing configured to receive a rotational force from the driver assembly and to transmit the rotational force to the cartridge assembly, the cartridge assembly comprising a fluid reservoir and a plunger assembly slidably disposed in the fluid reservoir, the cartridge assembly engaged with a bone penetrating needle and configured to rotate to insert the bone penetrating needle into the bone marrow;
    a plunger operating assembly configured to receive a portion of the plunger assembly of the cartridge assembly;
    a retractable sleeve configured to displace longitudinally relative to the drive housing and the plunger operating assembly, the retractable sleeve configured to move from a first position to a second position;
    a first spring configured to bias the retractable sleeve in the first position;
    a second spring configured to move the plunger operating assembly such that the plunger operating assembly moves the plunger assembly of the cartridge assembly to deliver the quantity of fluid to the bone marrow;
    a first release mechanism configured to release the second spring to move the plunger operating assembly; and
    a second release mechanism configured to release the engagement between the second portion of the drive housing and the cartridge assembly when the quantity of fluid is delivered to the bone marrow,
    wherein the first release mechanism releases the second spring to move the plunger operating assembly when the cartridge assembly is rotated to insert the bone penetrating needle into the bone marrow and the retractable sleeve is moved to its second position.

2. The apparatus of claim 1, where the first release mechanism comprises a pawl latch, the pawl latch configured to move from a first position to a second position that releases the second spring to move the plunger operating assembly,
    wherein the retractable sleeve comprises a ramp formed on an inner surface of the retractable sleeve, the ramp configured to move the pawl latch from its first position to its second position when the cartridge assembly is rotated to insert the bone penetrating needle into the bone marrow and the retractable sleeve is moved to its second position.

3. The apparatus of claim 2, further comprising a third spring configured to bias the pawl latch in its first position.

4. The apparatus of claim 1, wherein the second release mechanism comprises one or more balls configured to displace radially between a first position and a second position,
the one or more balls configured to maintain the engagement between the second portion of the drive housing and the cartridge assembly when the one or more balls are in the first position,
the one or more balls configured to release the engagement between the second portion of the drive housing and the cartridge assembly when the one or more balls are in the second position.

5. The apparatus of claim 4, wherein the retractable sleeve comprises one or more recesses formed on an inner surface of the retractable sleeve, each recess configured to receive a ball of the one or more balls to allow the ball to displace radially from the first position to the second position.

6. The apparatus of claim 4, wherein the second release mechanism further comprises one or more latch components configured to displace from a first position and a second position,
wherein the one or more latch components cooperate with the one or more balls to maintain the engagement between the second portion of the drive housing and the cartridge assembly when the one or more latch components and the one or more balls are in their first positions,
wherein the one or more latch components cooperate with the one or more balls to release the engagement between the second portion of the drive housing and the cartridge assembly when the one or more latch components and the one or more balls are in their second positions.

7. The apparatus of claim 6, wherein the plunger assembly of the cartridge assembly comprises one or more recesses formed on an outer surface of the plunger assembly, each recess configured to receive a ball of the one or more balls to allow the ball to displace radially from the first position to the second position.

8. The apparatus of claim 1, wherein the driver assembly comprises a motor and a drive shaft coupled to and extending from the motor,
wherein the first portion of the drive housing comprising an opening configured to receive a portion of the drive shaft.

9. An apparatus for delivering a quantity of fluid to bone marrow comprising:
a housing;
a motor disposed in the housing;
a drive shaft coupled to and extending from the motor;
a drive housing comprising a first portion configured to engage the drive shaft and a second portion configured to engage a cartridge assembly, the drive housing configured to receive a rotational force from the drive shaft and to transmit the rotational force to the cartridge assembly, the cartridge assembly comprising a fluid reservoir and a plunger assembly slidably disposed in the fluid reservoir, the cartridge assembly engaged with a bone penetrating needle and configured to rotate to insert the bone penetrating needle into the bone marrow;
a plunger operating assembly configured to receive a portion of the plunger assembly of the cartridge assembly;
a retractable sleeve configured to displace longitudinally relative to the drive housing and the plunger operating assembly, the retractable sleeve configured to move from a first position to a second position;
a first spring configured to bias the retractable sleeve in the first position;
a second spring configured to move the plunger operating assembly such that the plunger operating assembly moves the plunger assembly of the cartridge assembly to deliver the quantity of fluid to the bone marrow;
a first release mechanism configured to release the second spring to move the plunger operating assembly; and
a second release mechanism configured to release the engagement between the second portion of the drive housing and the cartridge assembly when the quantity of fluid is delivered to the bone marrow,
wherein the first release mechanism releases the second spring to move the plunger operating assembly when the cartridge assembly is rotated to insert the bone penetrating needle into the bone marrow and the retractable sleeve is moved to its second position.

10. The apparatus of claim 9, wherein the drive housing, the first spring, and the second spring are disposed in portions of the housing,
wherein a portion of the retractable sleeve extends from an opening in the housing.

11. The apparatus of claim 10, wherein the housing comprises a handle,
wherein the handle comprises a trigger,
wherein the trigger is configured to activate the motor to rotate the drive shaft.

12. The apparatus of claim 9, where the first release mechanism comprises a pawl latch, the pawl latch configured to move from a first position to a second position that releases the second spring to move the plunger operating assembly,
wherein the retractable sleeve comprises a ramp formed on an inner surface of the retractable sleeve, the ramp configured to move the pawl latch from its first position to its second position when the cartridge assembly is rotated to insert the bone penetrating needle into the bone marrow and the retractable sleeve is moved to its second position.

13. The apparatus of claim 12, further comprising a third spring configured to bias the pawl latch in its first position.

14. The apparatus of claim 12, wherein the retractable sleeve comprises a reduced diameter portion and an enlarged diameter portion with a shoulder portion formed between the reduced diameter portion and the enlarged diameter portion,
wherein the ramp is formed on an inner surface of the enlarged diameter portion proximate to the shoulder portion.

15. The apparatus of claim 9, wherein the second release mechanism comprises one or more balls configured to displace radially between a first position and a second position,
the one or more balls configured to maintain the engagement between the second portion of the drive housing and the cartridge assembly when the one or more balls are in the first position,
the one or more balls configured to release the engagement between the second portion of the drive housing and the cartridge assembly when the one or more balls are in the second position.

16. The apparatus of claim 15, wherein the retractable sleeve comprises one or more recesses formed on an inner surface of the retractable sleeve, each recess configured to receive a ball of the one or more balls to allow the ball to displace radially from the first position to the second position.

17. The apparatus of claim 9, wherein the portion of the retractable sleeve that extends from the opening in the housing comprises a window.

18. The apparatus of claim 9, wherein at least the portion of the retractable sleeve that extends from the opening in the housing is formed of a transparent material.

19. An apparatus for delivering a quantity of fluid to bone marrow comprising:
- a drive housing comprising a first portion configured to engage a driver assembly and a second portion configured to engage a cartridge assembly, the drive housing configured to receive a rotational force from the driver assembly and to transmit the rotational force to the cartridge assembly, the cartridge assembly comprising a fluid reservoir and a plunger assembly slidably disposed in the fluid reservoir, the cartridge assembly engaged with a bone penetrating needle and configured to rotate to insert the bone penetrating needle into the bone marrow;
- a plunger operating assembly configured to receive a portion of the plunger assembly of the cartridge assembly, the plunger operating assembly further configured to move when the cartridge assembly is rotated to insert the bone penetrating needle into the bone marrow;
- a first release mechanism configured to permit the plunger operating assembly to move from a retracted position to a released position;
- a second release mechanism configured to release the engagement between the second portion of the drive housing and the cartridge assembly when the quantity of fluid is delivered to the bone marrow; and
- a spring loaded retractable sleeve configured to displace longitudinally relative to the drive housing and the plunger operating assembly, the retractable sleeve configured to move from an extended position to a retracted position;

wherein the plunger operating assembly is configured to move the plunger assembly of the cartridge assembly to deliver the quantity of fluid to the bone marrow when the plunger operating assembly is moved to the released position and the retractable sleeve is moved to the retracted position.

20. The apparatus of claim 19, wherein the second release mechanism is further configured to maintain a positive engagement between the drive housing and the cartridge assembly until after the plunger assembly of the cartridge assembly has moved from a first position to a second position such that the quantity of fluid contained in the cartridge assembly is injected at a target site before disengagement of the cartridge assembly from the drive housing.

* * * * *